United States Patent
Cima et al.

(10) Patent No.: US 11,344,217 B2
(45) Date of Patent: May 31, 2022

(54) NMR SENSOR AND METHODS FOR RAPID, NON-INVASIVE DETERMINATION OF HYDRATION STATE OR VASCULAR VOLUME OF A SUBJECT

(71) Applicant: Massachusetts Institute of Technology, Cambridge, MA (US)

(72) Inventors: Michael J. Cima, Winchester, MA (US); Matthew Li, Somerville, MA (US); Christophoros C. Vassiliou, El Cerrito, CA (US); Negar Tavassolian, Hoboken, NJ (US); Lina Avancini Colucci, Lexington, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 603 days.

(21) Appl. No.: 14/896,806

(22) PCT Filed: Sep. 5, 2014

(86) PCT No.: PCT/US2014/054344
§ 371 (c)(1),
(2) Date: Dec. 8, 2015

(87) PCT Pub. No.: WO2015/035205
PCT Pub. Date: Mar. 12, 2015

(65) Prior Publication Data
US 2016/0120438 A1    May 5, 2016

Related U.S. Application Data

(60) Provisional application No. 61/874,156, filed on Sep. 5, 2013.

(51) Int. Cl.
*A61B 5/055* (2006.01)
*G01R 33/50* (2006.01)
(Continued)

(52) U.S. Cl.
CPC ............... *A61B 5/055* (2013.01); *A61B 5/02* (2013.01); *A61B 5/443* (2013.01); *A61B 5/4875* (2013.01);
(Continued)

(58) Field of Classification Search
CPC .... G01R 33/383; G01R 33/50; G01R 33/448; G01R 33/4608; A61B 5/055;
(Continued)

(56) References Cited

U.S. PATENT DOCUMENTS 5,064,638 A * 11/1991 Moore ................ G01R 33/446
324/307
6,067,802 A 5/2000 Alonso
(Continued)

FOREIGN PATENT DOCUMENTS

| KR | 100680699 B1 | 2/2007 |
| WO | WO-2012/07095 A1 | 5/2012 |
| WO | WO-2013/046158 A2 | 4/2013 |

OTHER PUBLICATIONS

Sinclair et al., Test-Retest Reproducibility of MTR, T2 and 3-point Dixon Fat Quantification Methods in Muscle MRI, Proc. Intl. Soc. Mag. Reson. Med. 18, 2010.*
(Continued)

*Primary Examiner* — Bo Joseph Peng
(74) *Attorney, Agent, or Firm* — Clark & Elbing LLP

(57) ABSTRACT

The invention features methods for detecting the hydration state or vascular volume of a subject using a device capable of nuclear magnetic resonance (NMR) measurement. The methods involve exposing a portion of a tissue of the subject in vivo to a magnetic field and RF pulse from the device to excite hydrogen nuclei of water within the tissue portion, and measuring a relaxation parameter of the hydrogen nuclei in the tissue portion, the relaxation parameter being a
(Continued)

quantitative measure of the hydration state or vascular volume of the subject as a whole. The invention also features devices and computer-readable storage media for performing the methods of the invention.

20 Claims, 13 Drawing Sheets

(51) Int. Cl.
    *G01R 33/383*     (2006.01)
    *A61B 5/00*     (2006.01)
    *A61B 5/02*     (2006.01)
    *G01R 33/44*     (2006.01)
    *G01R 33/46*     (2006.01)
    *A61B 5/145*     (2006.01)

(52) U.S. Cl.
    CPC .......... *A61B 5/6826* (2013.01); *G01R 33/383* (2013.01); *G01R 33/448* (2013.01); *G01R 33/4608* (2013.01); *G01R 33/50* (2013.01); *A61B 5/14535* (2013.01); *A61B 5/14542* (2013.01); *A61B 2560/0431* (2013.01)

(58) Field of Classification Search
    CPC ......... A61B 5/4875; A61B 5/02; A61B 5/443; A61B 5/6826; A61B 5/14535; A61B 5/14542; A61B 2560/0431
    See application file for complete search history.

(56) References Cited

U.S. PATENT DOCUMENTS

| | | |
|---|---|---|
| 6,278,891 B1 | 8/2001 | Reiderman et al. |
| 7,026,712 B2 | 4/2006 | Hayashi et al. |
| 7,736,354 B2 | 6/2010 | Gelfand et al. |
| 8,457,798 B2 | 6/2013 | Hackett |
| 2004/0030240 A1 | 2/2004 | Kimura |
| 2004/0140800 A1 | 7/2004 | Madio et al. |
| 2005/0029193 A1* | 2/2005 | Matson ................. A61M 1/342 210/645 |
| 2005/0148858 A1 | 7/2005 | Hargreaves |
| 2006/0083689 A1* | 4/2006 | Haroon ................. A61K 49/085 424/9.351 |
| 2008/0108894 A1* | 5/2008 | Elgavish ............... G06T 7/0012 600/420 |
| 2009/0128272 A1 | 5/2009 | Hills |
| 2010/0267741 A1* | 10/2010 | Penrose ............... C07D 231/14 514/254.05 |
| 2010/0308822 A1* | 12/2010 | Prado ..................... G01N 24/08 324/309 |
| 2011/0087087 A1* | 4/2011 | Peacock, III .......... A61B 5/055 600/410 |
| 2012/0223705 A1 | 9/2012 | Lowery et al. |
| 2013/0096415 A1* | 4/2013 | Ruff .................... A61B 5/14546 600/410 |

OTHER PUBLICATIONS

Shibahara et al., Water Fat Separation Using the Single Acquisition "Sandwich" Type 3-Point Dixon Method to Optimize Knee Joint Scans, Nagoya J. Med. Sci. 63. 41-49, 2000.*
Leydon et al., The role of hydration in vocal fold physiology, Curr Opin Otolaryngol Head Neck Surg. Jun. 2010; 18(3): 171-175.*
Mulkern et al., Osmotic Effects on the T2 Relaxation Decay of In Vivo Muscle, Magnetic Resonance in Medicine, 46:592-599, 2001.*
Stefanacci et al., Understanding Clinical Dehydration and Its Treatment, J Am Med Dir Assoc, 2008; 9: 292-301.*
Marsh et al., Effects of exercise on muscle transverse relaxation determined by MR imaging and in vivo relaxometry, J. Appl. Physiol., 88: 226-233, 2000.*
Science Guys, What is nuclear magnetic resonance (NMR), and how does it work?, Feb. 2003; https://www.uu.edu/dept/physics/scienceguys/2003Feb.cfm.*
Ghiassi-Nejad et al., Proton spin}spin relaxation study of molecular dynamics and proteoglycan hydration in articular cartilage, Biomaterials 21 (2000) 2089-2095.*
Michael W. Hasz, Review Article Diagnostic Testing for Degenerative Disc Disease, Advances in Orthopedics vol. 2012, Article ID 413913, 7 pages, Published Jul. 12, 2012.*
Wang et al., Evaluation of Iron Overload by Single Voxel MRS Measurement of Liver T2, J. Magn. Reson. Imaging 2002;15:395-400.*
Kim et al., Fast Multi-voxel Two-dimensional Spectroscopic Imaging at 3T, Magn Reson Imaging. Oct. 2007; 25(8): 1155-1161.*
"Guideline Summary NGC-9468: Oral Rehydration Therapy (ORT) in Children," <http://www.guideline.gov/content.aspx?id=38900>, retrieved on Jan. 12, 2016 (5 pages).
Adlbrecht et al., "Chronic heart failure leads to an expanded plasma volume and pseudoanaemia, but does not lead to a reduction in the body's red cell volume," Eur Heart J. 29(19):2343-50 (2008).
Androne et al., "Relation of unrecognized hypervolemia in chronic heart failure to clinical status, hemodynamics, and patient outcomes," Am J Cardiol. 93(10):1254-9 (2004).
Armstrong, "Assessing hydration status: the elusive gold standard," J Am Coll Nutr. 26(5 Suppl):575S-584S (2007).
Bertram et al., "Origin of multiexponential T(2) relaxation in muscle myowater," J Agric Food Chem. 49(6):3092-100 (2001).
Bonn et al., "Some applications of magnetic resonance imaging in fluid mechanics: complex flows and complex fluids," Annu. Rev. Fluid Meeh. 40:209-33 (2008).
Bruckner et al., "Fish oil increases peripheral capillary blood cell velocity in humans," Atherosclerosis 66(3):237-45 (1987).
Carter et al., Appendix D: Hydration Status Monitoring. *Monitoring Metabolic Status: Predicting Decrements in Physiological and Cognitive Performance*. National Academy of Sciences, 270-80 (2004).
Cheuvront et al., "Physiologic basis for understanding quantitative dehydration assessment," Am J Clin Nutr. 97(3):455-62 (2013).
Costanzo et al., "Treatment of congestion in heart failure with diuretics and extracorporeal therapies: effects on symptoms, renal function, and prognosis," Heart Fail Rev. 17(2):313-24 (2012) (13 pages).
Costill et al., "Muscle water and electrolytes following varied levels of dehydration in man," J Appl Physiol. 40(1):6-11 (1976) (7 pages).
Davies et al., "ABC of heart failure. Management: diuretics, ACE inhibitors, and nitrates," BMJ. 320(7232):428-31 (2000).
De Luca et al., "Congestion in acute heart failure syndromes: importance of early recognition and treatment," Rev Cardiovasc Med. 7(2):69-74 (2006).
Dehghan et al., "Is bioelectrical impedance accurate for use in large epidemiological studies?," Nutr J. 7:26 (2008) (7 pages).
Fagrell et al., "Effect of intravenously administered pindolol on skin capillary blood cell velocity in fingers," Br J Clin Pharmacol. 13(Suppl 2):233S-235S (1982).
Gasser, "Capillary blood cell velocity in finger nailfold: characteristics and reproducibility of the local cold response," Microvasc Res. 40(1):29-35 (1990).
Gheorghiade et al., "Assessing and grading congestion in acute heart failure: a scientific statement from the acute heart failure committee of the heart failure association of the European Society of Cardiology and endorsed by the European Society of Intensive Care Medicine," Eur J Heart Fail. 12(5):423-33 (2010).
Hills et al., "NMR studies of changes in subcellular water compartmentation in parenchyma apple tissue during drying and freezing," International Journal of Food Science and Technology. 32(1):51-61 (1997) (Abstract only) (1 page).
International Preliminary Report on Patentability for International Application No. PCT/US2014/054344, dated Mar. 8, 2016 (9 pages).
International Search Report and Written Opinion for International Patent Application No. PCT/US2014/054344, dated Jan. 8, 2015 (11 pages).

(56) References Cited

OTHER PUBLICATIONS

Jaffrin et al., "Body fluid volums measurements by impedance: A review of bioimpedance spectroscopy (BIS) and bioimpedance analysis (BIA) methods," Med Eng Phys. 30(10):1257-69 (2008).
Kamman et al., "Multi-exponential relaxation analysis with MR imaging and NMR spectroscopy using fat-water systems," Magn Reson Imaging. 5(5):381-92 (1987).
Kavouras, "Assessing hydration status," Curr Opin Clin Nutr Metab Care. 5(5):519-24 (2002).
Kenefick et al., Chapter 70: Dehydration and Rehydration. *Wilderness Medicine*. Elsevier, 71-82 and e70-1-e70-4 (2012).
Kim, "Preventable hospitalizations of dehydration: implications of inadequate primary health care in the United States," Ann Epidemiol. 17(9):736, Abstract P39 (2007).
Lilly, *Pathophysiology of Heart Disease, Fifth Edition*. Lippincott Williams & Wilkins, 478 pages (2011).
Makhoul et al., "Relation between changes in red cell distribution width and clinical outcomes in acute decompensated heart failure," Int J Cardiol. 167(4):1412-6 (2013).
Montgomery et al., "Monitoring intracellular, interstitial, and intravascular vol. changes during fluid management procedures," Med Biol Eng Comput. 51 (10):1167-75 (2013) (18 pages).
Nose et al., "Distribution of water losses among fluid compartments of tissues under thermal dehydration in the rat," Jpn J Physiol. 33(6):1019-29 (1983).
Peronnet et al., "Pharmacokinetic analysis of absorption, distribution and disappearance of ingested water labeled with $D_2O$ in humans," Eur J Appl Physiol. 112(6):2213-22 (2012).
Riley, "Acute decompensated heart failure: diagnosis and management," Br J Nurs. 22(22):1290-5 (2013).
Sasson et al., "Hypodermoclysis: an alternative infusion technique," Am Fam Physician. 64(9):1575-8 (2001).
Shirreffs, "Markers of hydration status," Eur J Clin Nutr. 57 Suppl 2:S6-9 (2003).
Sieck, Chapter 2: The Economics and Reimbursement of Congestive Heart Failure. *Short Stay Management of Acute Heart Failure*. Humana Press, 9-32 (2012).
Silvennoinen et al., "Effects of hematocrit and oxygen saturation level on blood spin-lattice relaxation," Magn Reson Med. 49(3):568-71 (2003).
Silverberg et al., "The importance of anemia and its correction in the management of severe congestive heart failure," Eur J Heart Fail. 4(6):681-6 (2002).
Stevenson, "Are hemodynamic goals viable in tailoring heart failure therapy? Hemodynamic goals are relevant," Circulation. 113(7):1020-33 (2006) (15 pages).
Stucker et al., "Capillary blood cell velocity in human skin capillaries located perpendicularly to the skin surface: measured by a new laser Doppler anemometer," Microvasc Res. 52(2):188-92 (1996).
Thomas et al., "Bioimpedance spectrometry in the determination of body water compartments: accuracy and clinical significance," Appl Radiat Isot. 49(5-6), 447-55 (1998).
Thomas et al., "Understanding clinical dehydration and its treatment," J Am Med Dir Assoc. 9(5):292-301 (2008).
Weitzman et al., "The clinical physiology of water metabolism. Part III: The water depletion (hyperosmolar) and water excess (hyposmolar) syndromes," West J Med. 132(1):16-38 (1980).
Whittall et al., "Quantitative interpretation of NMR relaxation data," J Magn Reson. 84:134-52 (1989).
Extended European Search Report for European Application No. 14841459.2, dated Mar. 29, 2017 (14 pages).
Communication pursuant to Article 94(3) EPC for European Patent Application No. 14841459.2, dated Oct. 31, 2019 (8 pages).
Communication pursuant to Article 94(3) EPC for European Patent Application No. 14841459.2, dated Jun. 5, 2020 (6 pages).
Bashyam et al., "Dehydration assessment via portable, single sided magnetic resonance sensor," Magn Reson Med. 00:1-15 (2019).
Cameron et al., "Characterization of Proton NMR Relaxation Times in Normal and Pathological Tissues by Correlation with Other Tissue Parameters," Magn Reson Imaging. 2(2):97-106 (1984).
Cheuvront et al., "Dehydration: Physiology, Assessment, and Performance Effects." Compr Physiol. 4(1):257-285 (2014).
Colucci et al., "Fluid assessment in dialysis patients by point-of-care magnetic relaxometry." Sci Transl Med. 11 (502):eeau1749 (2019) (15 pages).
Communication pursuant to Article 94(3) EPC for European Patent Application No. 14841459.2, dated Oct. 5, 2021 (8 pages).
Fukumoto et al., "Differences in Composition of Sweat Induced by Thermal Exposure and by Running Exercise," Clin Cardiol. 11 (10):707-709 (1988).
Li et al., "(1)H nuclear magnetic resonance (NMR) as a tool to measure dehydration in mice," NMR Biomed. 28(8):1:1031-1039 (2015).
Moser et al., "On the Correlation between Tissue Hydration State and Proton NMR Relaxation Rates in Experimental Liver Transplantation." NMR Biomed. 10(3):143-150 (1997).

* cited by examiner

NMR SENSOR AND METHODS FOR RAPID, NON-INVASIVE DETERMINATION OF HYDRATION STATE OR VASCULAR VOLUME OF A SUBJECT

STATEMENT AS TO FEDERALLY FUNDED RESEARCH

This invention was made with Government support under Contract No. W911NF-13-D-0001 awarded by the Army Research Office. The Government has certain rights in the invention.

FIELD OF THE INVENTION

In general, the present invention relates to methods and devices for rapid and non-invasive in vivo determination of hydration state or vascular volume of a subject.

BACKGROUND

Hydration state is a physiologic condition that can have profound implications for human health, including physical and cognitive performance (Kavouras, *Current Opinion in Clinical Nutrition and Metabolic Care* 5: 519-24, 2002). Euhydration (normal hydration) is a highly regulated state with less than 1% deviations from homeostatic norms in healthy individuals. Euhydration arises from a dynamic process in which an individual continually loses water through renal, cutaneous, respiratory, and gastrointestinal routes (Cheuvront et al., *The American Journal of Clinical Nutrition*, 97:455-62, 2013; Weitzman et al., *West. J. Med.* 131:373-409, 1980; Kim, *Annals of Epidemiology*, 17:736, 2007) and typically regains water through fluid and food ingestion. Compromises in fluid regulation leads to decline in physical and cognitive performance proportional to the amount of water lost (Carter et al. *Hydration Status Monitoring*, Book Chapter; National Academy of Science, 2004).

Two main water imbalances exist: hypernatremia (dehydration) and hyponatremia (water intoxication). Hypernatremia is defined as elevated serum sodium concentration. This may occur due to excessive water loss (e.g., sweating) without supplementary fluid intake or by inherent pathology, such as deterioration of hypothalamic thirst centers, which occurs in, e.g., the elderly. These losses in water effectively deplete intracellular and extracellular fluid compartments. Hyponatremia is defined as decreased serum sodium concentrations and may be due to various conditions, including salt depletion, renal failure, and congestive heart failure, in which excess water results in diluted salt and electrolyte concentrations (Weitzman et al., *West. J. Med.* 131:373-409, 1980).

Hydration imbalance can mean either dehydration or over-hydration, both of which may affect cognitive and physical performance. The number of hospitalizations for dehydration has increased steadily in recent decades, reaching 518,000 hospitalizations and $5.5 billion in hospital charges in 2004 (Kim, *Annals of Epidemiology*, 17:736, 2007). Dehydration negatively impacts cardiovascular functioning, compromises thermoregulation, and decreases exercise performance (Cheuvront et al., *the American Journal of Clinical Nutrition*, 97:455-62, 2013). Over-hydration may arise from a variety of underlying conditions including renal failure and congestive heart failure (CHF). CHF is a chronic, age-related disease with an estimated 670,000 new cases per year. CHF patients took up 6.5 million annual hospital days and represented $39.2 billion in health costs (of which hospital costs accounted for 60%) in 2010 (Sieck, *The Economics and Reimbursement of Congestive Heart Failure*, Chapter 2, 2012).

One particular example of hydration imbalance is congestion. Fluid is retained in the body (termed congestion), particularly in the liver, lungs, hands, and feet, as the heart loses its pumping power. The first sign of congestion is high left ventricular (LV) filling pressure followed by clinical symptoms like peripheral edema, dyspnea, orthopnea (shortness of breath while laying down), exercise intolerance, pathologic S3 or S4 heart sounds, tachycardia and tachypenia, and jugular venous distention (JVD) (see, e.g., *Pathophysiology of Heart Disease*, Lippincott Williams & Wilkins, 2011, doi:10.1016/B978-008043924-2/50055-9; De Luca et al., *Rev. Cardiovasc. Med.*, 7:69-74, 2006; Sieck in *Short Stay Manag. Acute Hear. Fail.*, Chapter 2; ed. Peacock, W. F.; Humana Press, 2012; Riley, *Br. J. Nurs.*, 22:1290-1295, 2013; and Stevenson, *Circulation*, 113:1020-1027, discussion 1033, 2006). The majority of HF hospitalizations are related to clinical congestion, but assessment methods like echocardiogram, electrocardiogram, typically measure cardiac function and cardiac output. It is important to perform these measurements to uncover the underlying cause of a patient's heart failure. It is also important to assess congestion because it is thought that untreated volume overload is one of the main reasons for early readmission (De Luca et al., *Rev. Cardiovasc. Med.*, 7:69-74, 2006). Severe congestion is associated with increase in 60-day mortality risk of 8.1% versus 4.9% in patients without severe congestion. Early identification of hemodynamic congestion, before clinical manifestations are present could reduce need for hospital admission and readmission (De Luca et al., *Rev. Cardiovasc. Med.*, 7:69-74, 2006). Increased volume can, however, be difficult to recognize when common signs and symptoms of clinical congestion are not manifested during an acute exacerbation (Androne et al., *Am. J. Cardiol.*, 93:1254-1259, 2004). Patients are often discharged when their symptoms improve but symptoms are poor predictors of elevated LV filling pressures. Congestion is an essential evaluative and therapeutic metric in heart failure patients that should be assessed for every patient. Multiple manifestations of congestion are, therefore, important to measure—such as edema and increased blood volume—to get a more complete picture of a patient's congestion status (De Luca et al., *Rev. Cardiovasc. Med.*, 7:69-74, 2006).

Many patients with heart failure (HF) are anemic either due to reduced hemoglobin quantity (true anemia) or increased plasma volume and, therefore, reduced hemoglobin concentration (called hemodilution) (Montgomery et al., *Med. Biol. Eng. Comput.* C, 2013; Silverberg et al., *Eur. J. Heart Fail.*, 4:681-686, 2002; Adlbrecht et al., *Eur. Heart J.*, 29:2343-2350, 2008; Makhoul et al., *Int. J. Cardiol.*, 167:1412-1416, 2013; and Silvennoinen et al., *Magn. Reson. Med.*, 49:568-571, 2003). Hemodilution is associated with poor prognosis. Patients with hemodilution tend to do worse than patients with true anemia, which means that volume overload is an important predictor of poor outcome (Makhoul et al., *Int. J. Cardiol.*, 167:1412-1416, 2013). Pulmonary Capillary Wedge Pressure (PCWP) is the gold standard for assessing hemocongestion and is significantly higher ($p<0.01$) in patients with hemodilution. However, catheterization, despite accuracy, carries risks of disturbance of plaque, vessel or ventricle puncture, embolization leading to myocardial infarction or stroke (Gheorghiade et al., *Eur. J. Heart Fail.*, 12:423-433, 2010). Patients are generally discharged when their symptoms improve, which does not necessarily mean their underlying volume overload has been treated. It is thought that untreated volume overload is the reason for frequent hospital readmissions (*Pathophysiology of Heart Disease,* Lippincott Williams & Wilkins, 2011).

Hydration imbalances are prime examples of conditions for which hospitalization may be prevented if they are diagnosed and managed early. Unfortunately, an individual's hydration state is difficult to assess, and currently there is no single, universal gold standard method to determine hydration state to inform decision making (Kavouras, *Current Opinion in Clinical Nutrition and Metabolic Care* 5:519-524, 2002). Often, multiple metrics are used in combination to provide a more complete assessment of hydration state. The most widely used metrics include: body mass change, plasma osmolality, % plasma volume change, urine osmolality, urine specific gravity, urine conductivity, urine color, total body water (dilutional), and total body water (bioelectric impedance) (U.S. Pat. No. 7,736,354; Shirreffs, *European Journal of Clinical Nutrition,* 57 Suppl. 2:S6-9, 2003; Jaffrin, *Medical Engineering & Physics,* 30:1257-69, 2008; Thomas et al., *Applied radiation and isotopes: including data, instrumentation and methods for use in agriculture, industry and medicine,* 49(5-6), 447-55, 1998, Montgomery et al., *Medical & biological engineering & computing,* c. doi:10.1007/s11517-013-1064-3, 2013; Dehghan, *Nutrition Journal,* 9:7-26, 2008; Carter et al. *Hydration Status Monitoring,* Book Chapter; National Academy of Science, 2004; Armstrong, *Journal of the American College of Nutrition,* 26:575S-585S, 1997). These tools and metrics are plagued with issues including high variability, the presence of confounding factors, and poor reliability when used as a stand-alone measurement (Carter at al. *Hydration Status Monitoring,* Book Chapter; National Academy of Science, 2004; Armstrong, *Journal of the American College of Nutrition,* 26:575S-585S, 1997).

None of the methods described above provides a quantitative assessment of the overall hydration state or vascular volume of a subject. Instead, only visual and/or qualitative confirmation of a hydration state is available through these methods.

There exists a need for rapid, accurate, non-invasive techniques and devices for measuring overall hydration state and/or vascular volume of a subject, particularly in an outpatient setting. Such a technique could be used in diagnosing, monitoring, and treating a patient at risk of hydration imbalances, including, e.g., the elderly, CHF patients, athletes, and military personnel.

SUMMARY OF THE INVENTION

The present invention relates to the use of nuclear magnetic resonance (NMR) in assessing a hydration state or vascular volume in a tissue portion of a subject. NMR is a physical phenomenon in which nuclei of interest are exposed to and interact with applied magnetic fields, rendering the relative energies of nuclei having opposing spins non-degenerate. Excitation (perturbation) of nuclei in a lower energy spin state leads to a change in their spin state to a higher energy state. The time required for the nuclei to return to equilibrium, after perturbation, is known as the relaxation time, which can be measured using methods and devices of the present invention to determine the hydration state and/or vascular volume of a subject.

In one aspect, the invention provides a method for non-invasively determining a hydration state of a subject using a device capable of nuclear magnetic resonance (NMR) measurement; the method involves: (a) exposing a portion of a tissue of the subject in vivo to a magnetic field and RF pulse from the device to excite hydrogen nuclei of water within the tissue portion, and (b) measuring a relaxation parameter of the hydrogen nuclei in the tissue portion, where the relaxation parameter is a quantitative measure of the hydration state of the subject.

In the same aspect, the invention provides a method for non-invasively determining a vascular volume of a subject using a device capable of nuclear magnetic resonance (NMR) measurement; the method involves: (a) exposing a portion of a tissue of the subject in vivo to a magnetic field and RF pulse from the device to excite hydrogen nuclei of water within the tissue portion, and (b) measuring a relaxation parameter of the hydrogen nuclei in the tissue portion, where the relaxation parameter provides a quantitative measure of the vascular volume of the subject.

In the same aspect, the invention provides a method for non-invasively determining a fluid volume in one or more water compartments in a subject (e.g., an intracellular, an interstitial, an extracellular, or a vascular compartment) using a device capable of nuclear magnetic resonance (NMR) measurement; the method involves: (a) exposing a portion of a tissue of the subject in vivo to a magnetic field and RF pulse from the device to excite hydrogen nuclei of water within the tissue portion, and (b) measuring a relaxation parameter of the hydrogen nuclei in the tissue portion, where the relaxation parameter provides a quantitative measure of the fluid volume in one or more water compartments of the subject (e.g., an intracellular, an interstitial, an extracellular, or a vascular compartment).

In some embodiments of the methods of the invention, the hydration state of an intracellular, an interstitial, an extracellular, or a vascular compartment of the tissue portion is measured. In certain embodiments, the hydration state of the vascular compartment is measured. In certain embodiments, the tissue portion comprises an intracellular, interstitial, extracellular, or vascular compartment, or a combination thereof. In particular embodiments, the tissue portion comprises the vascular compartment. In some embodiments, the tissue portion comprises a lean tissue (e.g., the NMR measurement is carried out on a lean tissue). In other embodiments, the tissue portion comprises an adipose tissue (e.g., the NMR measurement is carried out on an adipose tissue). In further embodiments, the water is free water or water bound to macromolecules.

In other embodiments of the methods of the invention, the measuring further includes data deconvolution, single exponential regression analysis, and/or multi-exponential regression analysis. In some embodiments of the methods of the invention, an increase in the relaxation parameter relative to a reference measurement indicates an increased hydration level of the subject or a decrease in the relaxation parameter relative to a reference measurement indicates a decreased hydration level of the subject. In some embodiments of the methods of the invention, an increase in the relaxation parameter relative to a reference measurement indicates an increased vascular volume of the subject or a decrease in the relaxation parameter relative to a reference measurement indicates a decreased vascular volume of the subject. In certain embodiments of the methods of the invention, the data deconvolution includes producing a spectrum having one or more peaks corresponding to one or more water compartments. In particular embodiments, the one or more water compartments is an intracellular, an interstitial, an extracellular, or a vascular compartment. In specific embodiments, the one or more water compartments is a vascular compartment.

In some embodiments of the methods of the invention, the reference measurement includes one or more prior measurements of the relaxation parameter of hydrogen nuclei of water in the tissue portion of the subject. In other embodiments, the reference measurement includes one or more measurements of the relaxation parameter of hydrogen nuclei of water in the tissue portion of a population of reference subjects. In certain embodiments, the reference subjects have a known hydration state. In particular embodiments, the known hydration state is euhydration.

In other embodiments, the subject is human. In certain embodiments of the methods of the invention, the subject has or is at risk of having a hydration imbalance. In particular embodiments of the methods of the invention, the hydration imbalance is hyponatremia, or hypernatremia. In other embodiments of the methods of the invention, the hydration imbalance is hypokalemia or hyperkalemia.

In some embodiments of the methods of the invention, the subject is selected from the group consisting of an elderly subject, a child, an athlete, a soldier, an aircraft pilot, an air traffic controller, a locomotive engineer, and a crane operator. In other embodiments, the subject has a disease or condition that increases the risk of having, or results from, hydration imbalance. In certain embodiments, the subject has a disease or condition selected from the group consisting of congestive heart failure (CHF), renal failure, liver cirrhosis, nephrotic syndrome, brain swelling, diabetes, staphylococcal infection, nephrolithiasis, diarrhea, colitis, preferably ulcerative colitis, pyelonephritis, cystic fibrosis, Huntington's disease, rotavirus infection, herpangina, salmonellosis, norovirus infection, pertussis, cryptosporidium infection, cholera, coma, and water intoxication. In particular embodiments, the subject has, or is suspected of having, congestion or hemodilution. In certain embodiments, the subject has at least one symptom of congestion selected from the group consisting of dyspnea, othopnea, exercise intolerance, pathologic S3 or S4 heart sounds, tachycardia, tachypenia, jugular venous distention, peripheral edema, ascites, and increased filling pressures of the heart. In other embodiments, the subject has congestive heart failure, liver failure, renal failure, Cushing's syndrome, or pulmonary congestion.

In some embodiments of the methods of the invention, the tissue portion has reduced blood flow relative to other tissues in the subject. In certain embodiments, the tissue portion is a peripheral body part. In particular embodiments, the tissue portion is or is within a finger, an ear, a nose, a cheek, a toe, a foot, a calf, a hand, a wrist, a leg, or an arm.

In other embodiments of the methods of the invention, the steps (a) and (b) are repeated two or more times. In some embodiments of the methods of the invention, the method is performed in the absence of a contrast agent.

In certain embodiments of the methods of the invention, the method involved single-voxel spectroscopy (SVS). In other embodiments, the method involves multi-voxel spectroscopy.

In some embodiments of the methods of the invention, the method is performed on a tissue volume of at least 0.01 $cm^3$. In certain embodiments, the method is performed on a tissue volume of at least 0.05 $cm^3$. In particular embodiments, the method is performed on a tissue volume of at least 0.1 $cm^3$. In other embodiments, the method is performed on a tissue volume of at most 20.0 $cm^3$. In certain embodiments, the method is performed on a tissue volume of at most 10.0 $cm^3$. In particular embodiments, the method is performed on a tissue volume of at most 5.0 $cm^3$. In specific embodiments, the method is performed on a tissue volume of about 3.3 $cm^3$. In other embodiments of the methods of the invention, the device is configured to provide a signal-to-noise ratio of greater than 5 from measurement of the relaxation parameter of the hydrogen nuclei of water in the tissue volume (e.g., any of the tissue volumes described herein). In some embodiments of the methods of the invention, the device is configured to provide a substantially homogeneous magnetic field over the volume (e.g., any of the tissue volumes described herein).

In particular embodiments of the methods of the invention, the relaxation parameter is a $T_2$ relaxation time, a $T_1$ relaxation time, a $T_{1\rho}$ relaxation time, or a $T_2^*$ relaxation time. In some embodiments, the relaxation parameter is a $T_2$ relaxation time, a $T_1$ relaxation time, or a $T_2^*$ relaxation time. In other embodiments, the relaxation parameter is a peak height of a relaxation signal or a peak width of a relaxation signal. In certain embodiments, the relaxation parameter is an area under a peak of a relaxation signal.

In some embodiments of the methods of the invention, the device is configured to be in close proximity to the tissue of the subject. In other embodiments, the device includes a surface, the surface being within at most 20 cm of the tissue of the subject. In certain embodiments, the surface is within at most 10 cm of the tissue of the subject. In particular embodiments, the surface is within at most 5 cm of the tissue of the subject. In specific embodiments of the methods of the invention, the surface is substantially in contact with the tissue of the subject.

In some embodiments, the device is portable. In certain embodiments, the device is hand-held. In other embodiments, the device is wearable. In particular embodiments, the device is attached to the tissue portion.

In some embodiments of the methods of the invention, the device includes (a) one or more magnets, (b) an RLC circuit, and (c) a processor. In some embodiments, the processor is capable of (i) determining relaxation time of the hydrogen nuclei and (ii) comparing the determined relaxation time to a reference time value.

In another aspect, the invention provides a device configured for measurement of a hydration state of a subject using nuclear magnetic resonance (NMR). The device includes: (a) one or more magnets, (b) an RLC circuit, and (c) a processor. The device is capable of performing an NMR measurement of a relaxation parameter of hydrogen nuclei in water in a tissue portion of the subject. The device is configured to provide a substantially homogeneous magnetic field over a tissue volume of at least 0.01 $cm^3$.

In the same aspect, the invention provides a device configured for measurement of a vascular volume of a subject using nuclear magnetic resonance (NMR); the device includes: (a) one or more magnets, (b) an RLC circuit, and (c) a processor, where the device is capable of performing an NMR measurement of a relaxation parameter of hydrogen nuclei in water in a tissue portion of the subject, and the device is configured to provide a substantially homogeneous magnetic field over a volume of at least 0.01 $cm^3$.

In some embodiments of the devices of the invention, the processor is capable of quantifying the hydration state of the subject.

In some embodiments of the devices of the invention, the processor is capable of converting the relaxation parameter of hydrogen nuclei in water in the portion of the tissue of the subject into the hydration state of the subject through a data deconvolution, a single-exponential regression analysis, or a multi-exponential regression analysis.

In some embodiments of the devices of the invention, the data deconvolution provides a relaxogram having the data resolved as a function of relaxation time and signal intensity.

In some embodiments of the methods of the invention, the processor is capable of quantifying the vascular volume of the subject. In certain embodiments, the processor is capable of converting the relaxation parameter of hydrogen nuclei in water in the portion of the tissue of the subject into the vascular volume of the subject through a data deconvolution, a single-exponential regression analysis, or a multi-exponential regression analysis. In particular embodiments, the data deconvolution provides a relaxogram having the data resolved as a function of relaxation time and signal intensity.

In other embodiments of the devices of the invention, the device is configured to provide a substantially homogeneous magnetic field over a volume of at least 0.05 cm$^3$. In certain embodiments, the device is configured to provide a substantially homogeneous magnetic field over a volume of at least 0.1 cm$^3$. In particular embodiments, the device is configured to provide a substantially homogeneous magnetic field over a volume of at most 20.0 cm$^3$. In specific embodiments, the device is configured to provide a substantially homogeneous magnetic field over a volume of at most 10.0 cm$^3$. In some embodiments, the device is configured to provide a substantially homogeneous magnetic field over a volume of at most 5.0 cm$^3$. In certain embodiments of the devices of the invention, the device is configured to provide a substantially homogeneous magnetic field over a volume of about 3.3 cm$^3$. In particular embodiments of the devices of the invention, the device is configured to provide signal-to-noise ratio greater than about 5 from measurement on a tissue volume of at least 0.01 cm$^3$.

In some embodiments of the devices of the invention, the device is configured to provide signal-to-noise ratio greater than about 5 from measurement on a tissue volume of at least 0.05 cm$^3$. In certain embodiments, the device is configured to provide signal-to-noise ratio greater than about 5 from measurement on a tissue volume of at least 0.1 cm$^3$. In particular embodiments, the device is configured to provide signal-to-noise ratio greater than about 5 from measurement on a tissue volume of at most 20.0 cm$^3$. In certain embodiments, the device is configured to provide signal-to-noise ratio greater than about 5 from measurement on a tissue volume of at most 10.0 cm$^3$. In some embodiments, the device is configured to provide signal-to-noise ratio greater than about 5 from measurement on a tissue volume of at most 5.0 cm$^3$. In specific embodiments, the device is configured to provide signal-to-noise ratio greater than about 5 from measurement on a tissue volume of about 3.3 cm$^3$.

In some embodiments of the devices of the invention, the processor is configured to analyze data from single-voxel spectroscopy (SVS). In other embodiments, the processor is configured to analyze data from multi-voxel spectroscopy.

In other embodiments of the devices of the invention, the device is configured to be in close proximity to the tissue of the subject. In some embodiments, the device includes a surface that is within at most 10 cm of the tissue of the subject. In certain embodiments, the device includes a surface that is within at most 5 cm of the tissue of the subject. In particular embodiments of the devices of the invention, the device includes a surface that is within at most 1 cm of the tissue of the subject. In specific embodiments of the devices of the invention, the device includes a surface that is substantially in contact with the tissue of the subject.

In some embodiments of the devices of the invention, the device is portable. In certain embodiments, the device is hand-held. In other embodiments, the device is wearable. In particular embodiments, the device is attached to the tissue portion.

In other embodiments of the devices of the invention, the relaxation parameter is selected from the group consisting of a $T_2$ relaxation time, a $T_1$ relaxation time, a $T_{1\rho}$ relaxation time, and a $T_2^*$ relaxation time. In some embodiments, the relaxation parameter is selected from the group consisting of a $T_2$ relaxation time, a $T_1$ relaxation time, and a $T_2^*$ relaxation time. In other embodiments of the devices of the invention, the relaxation parameter a peak height of a relaxation signal or a peak width of a relaxation signal. In certain embodiments of the devices of the invention, the relaxation parameter is an area under a peak of a relaxation signal.

In some embodiments of the devices of the invention, the one or more magnets are arranged to produce a central region containing the substantially homogeneous magnetic field. In other embodiments, the device includes 1-200 magnets. In particular embodiments, the device includes 2-200 magnets (e.g., 2-100 magnets, such as 72 magnets). In certain embodiments, the one or more magnets are independently selected from the list consisting of a permanent magnet, an electromagnet, and a pulsed electromagnet. In particular embodiments, the permanent magnet contains a rare earth metal. In further embodiments, the permanent magnet contains AlNiCo alloy. In particular embodiments, the permanent magnet contains a Nd alloy. In some embodiments, the Nd alloy is NdFeB alloy. In particular embodiments, the permanent magnet is N52 grade NdFeB alloy magnet. In other embodiments, the permanent magnet contains a Sm alloy. In some embodiments, the Sm alloy is SmCo alloy. In certain embodiments, the Sm alloy is SmCoFeCuZr alloy. In other embodiments, the permanent magnet has cuboidal shape. In certain embodiments, the permanent magnets are arranged in a Halbach array. In some embodiments, the electromagnet is a solenoid coil. In other embodiments, the electromagnet is a Helmholtz coil. In certain embodiments, the electromagnet is a Maxwell coil. In other embodiments, the electromagnet is a solenoid coil. In particular embodiments, the one or more magnets are arranged in a cylindrical or a polygonal shape. In yet other embodiments, the permanent magnet has a wedge shape.

In particular embodiments of the devices of the invention, the magnets generate a magnetic field strength that is at least 0.01 T. In other embodiments, the magnets generate a magnetic field strength of at least 0.1 T. In certain embodiments, the magnets generate a magnetic field strength of at least 0.2 T. In other embodiments, the magnets generate magnetic field strength of at most 2 T. In certain embodiments, the magnets generate magnetic field strength of at most 1 T. In particular embodiments, the magnets generate magnetic field strength of at most 0.5 T.

In certain embodiments of the methods of the invention, the magnets are held by one or more fixtures. In some embodiments, the one or more fixtures contains a non-magnetic or a minimally magnetic metal, a non-magnetic or a minimally magnetic alloy, a non-metal material, or combinations thereof. In certain embodiments, the non-metal material is selected from the group consisting of acetal copolymer, PTFE, PCTFE, ABS, Polycarbonate, PEEK, polypropylene, polystyrene, and blends thereof.

In other embodiments of the devices of the invention, the device further includes a temperature control system. In certain embodiments of the devices of the invention, the temperature control system is a closed-loop system. In particular embodiments, the temperature control system includes one or more temperature control elements and one or more electronic elements for thermal control. In some embodiments, the one or more temperature control elements are encased within one or more fixtures. In certain embodiments, the one or more fixtures further includes the one or more of electronic elements for thermal control. In particular embodiments, the device further includes a thermal insulation enclosure. In some embodiments, the device is kept at constant temperature between about 20° C. and about 50° C. (e.g., between about 30° C. and about 40° C.). In certain embodiments, the one or more fixtures further includes one or more of electronic elements for radiofrequency generation.

In some embodiments of the devices of the invention, the RLC circuit contains an inductor wire. In certain embodiments, the inductor wire is wrapped around a cylindrical element. In particular embodiments, the cylindrical element contains a material selected from the group consisting of acetal copolymer, PTFE, PCTFE, ABS, Polycarbonate, PEEK, glass, ceramics, and combinations thereof. In other embodiments, the inductor wire contains a metal selected from the group consisting of aluminum, copper, silver, and alloys thereof. In certain embodiments, the inductor wire is cylindrically enclosed within a non-conducting material. In particular embodiments, the inductor wire is 16 to 48 AWG (e.g., 32 AWG). In certain embodiments, the inductor wire is an insulated 32 AWG copper wire wrapped around an acetal copolymer cylindrical element.

In other embodiments of the devices of the invention, the device further includes a printed circuit board (PCB). In certain embodiments, the printed circuit board houses one or more variable capacitors. In particular embodiments, the one or more capacitors have capacitance of 1-30 pF. In other embodiments of the devices of the invention, the device further includes an enclosure for the PCB. In particular embodiments, the enclosure is made of electrically conductive material. In certain embodiments, the electrically conductive material is a metal (e.g., copper). In other embodiments, the device further includes an external connector. In some embodiments, the external connector connects the device to external power supply and controls. In certain embodiments, the external connector is a subminiature version A connector. In particular embodiments, the device further includes grounding. In other embodiments, the device further includes an amplifier. In certain embodiments, the device further includes a computer. In particular embodiments, the computer contains the processor. In specific embodiments, the device further includes a grounding element and a thermal control, where the one or more magnets are 72 cuboidal N52 NdFeB rare earth magnets arranged in a circular Halbach array, and where the device is configured to provide a substantially homogeneous magnetic field over a volume of about 3.3 cm³. In certain embodiments, the one or more magnets are 40 NdFeB rare earth magnets arranged in a circular Halbach array. In some embodiments, said magnets are wedge-shaped. In particular embodiments, the device contains two or more stacks of said magnets. In further embodiments, the device contains three or four stacks of the magnets.

In some embodiments of the devices of the invention, the tissue portion is a peripheral body part. In certain embodiments, the tissue portion is within a finger, an ear, a nose, a cheek, a toe, a foot, a calf, a hand, a wrist, a leg, or an arm.

In another aspect, the invention provides a computer-readable storage medium having stored thereon a computer program for converting a relaxation decay curve collected from an NMR measurement of a relaxation parameter of hydrogen nuclei in water in a tissue portion of a subject. The computer program includes a routine set of instructions for causing the computer to perform the steps of: (a) fitting a sum of one or more exponential curves to a measured decay curve, each exponential curve relating to one or more water compartments within the tissue portion of the subject, each of the one or more exponential curves having a first constant and a second constant, the first constant being a relaxation time of hydrogen nuclei in water within the one or more water compartments, the second constant being an intensity of a signal; (b) determining the first and the second constants from the fit; and (c) comparing the first, the second, or both constants to a reference first, second, or both constants.

In the same aspect, the invention provides a computer-readable storage medium having stored thereon a computer program for converting a relaxation decay curve collected from an NMR measurement of a relaxation parameter of hydrogen nuclei in water in a tissue portion of a subject, where the computer program contains a routine set of instructions for causing the computer to deconvolute raw relaxation data into a relaxogram, where the relaxogram having all resolvable components of the raw relaxation data as one or more peaks in a function of signal intensity and relaxation time. In certain embodiments, the computer program further contains a routine set of instructions for causing the computer to perform the steps of: (a) determining an area under the one or more peaks in the relaxogram; and (b) comparing the area to a reference peak area. In other embodiments, the computer program further contains a routine set of instructions for causing the computer to perform the steps of: (a) determining an intensity of the one or more peaks in the relaxogram; and (b) comparing the intensity (e.g., height or width) to a reference peak intensity.

Definitions

By "about," as used herein, is meant a value that is ±10% of the recited value.

By "hydration state" or "hydration status," as used interchangeably herein, is meant a state of body water content of a subject within a spectrum ranging from dehydration to euhydration to overhydration.

By "euhydration," as used herein, is meant a normal state of body water content of a subject, where the subject is not dehydrated or overhydrated. Daily fluctuation in body water content in a normal subject is about ±0.2-5% (e.g., ±0.2-2%) of the subject's body mass; thus, a subject having body water content within this range over short periods of time (e.g., minutes, hours, or days) is said to be in a state of euhydration. Other hydration state markers indicative of euhydration state of a human include serum osmolality (278-300 mOsmoles per kg of water), specific gravity of urine (1.003-1.020 g/mL), and urine osmolality (500-800 mOsmoles per liter of water).

By "dehydration," as used herein, is meant that a subject is in a state of hypernatremia. Hydration state markers indicative of dehydration of a human include, e.g., serum osmolality (greater than 300 mOsmoles per kg of water), specific gravity of urine (greater than 1.020 g/mL), and urine osmolality (greater than 800 mOsmoles per liter of water). Dehydration may also be assessed by urine color according to, e.g., Lucozade™ urine color chart (values equal to or greater than 4 correspond to a dehydration of a subject).

By "overhydration," as used herein, is meant that a subject is in a state of congestion or hyponatremia. Hydration state markers indicative of overhydration of a human include, e.g., serum osmolality (lower than 278 mOsmoles per kg of water), specific gravity of urine (lower than 1.003 g/mL), urine osmolality (lower than 500 mOsmoles per liter of water), increased weight due to fluid accumulation, peripheral edema, ascites, pulmonary edema, and others.

By "vascular volume" or "intravascular volume," as used interchangeably herein, is meant the volume of fluid in the circulatory system (e.g., in vessels, such as arteries, veins, and capillaries) of a subject.

By "hyponatremia," as used herein, is meant a condition of a subject in which the serum sodium levels are lower than 135 mEq/L. In severe cases of hyponatremia, the serum sodium levels are below 125 mEq/L.

By "hypernatremia," as used herein, is meant a condition of a subject in which the serum sodium levels exceed 145 mEq/L. In severe cases of hypernatremia, the serum sodium levels exceed 157 mEq/L.

By "hypokalemia," as used herein, is meant a condition of a subject in which the serum potassium levels are lower than 3.5 mEq/L.

By "hyperkalemia," as used herein, is meant a condition of a subject in which the serum potassium levels exceed 5.0 mEq/L.

By "subject," as used herein, is meant any animal, e.g., a mammal (e.g., a human).

By "non-invasive," as used herein, is meant without the need to break or puncture the skin or a mucous membrane of a subject or collect a bodily fluid or sample from the subject.

By "reduced blood flow," as used herein, is meant blood flow having a velocity lower than about 50 mm/s, preferably lower than 2 mm/s, and more preferably about, or lower than about, 1 mm/s. The blood velocity in tissues having reduced blood flow may be in the range of about 0.01 mm/s to about 50 mm/s, preferably in the range of about 0.01 mm/s to about 2 mm/s, more preferably in the range of about 0.1 mm/s to about 1 mm/s, or more preferably in the range of about 0.1 mm/s to about 0.5 mm/s, such as about 0.2 mm/s. For a description of reduced blood flow in tissues, see Gasser, *Microvascular Research*, 40:29-35, 1990; Bruckner et al., *Atherosclerosis*, 66:237-245, 1987; and Fagrell, *Br J Clin Pharmacol.*, 13:233S-235S, 1982.

By "substantially homogeneous magnetic field," as used herein, is meant a magnetic field having a homogeneity measure lower than about 500,000 ppm, e.g., in the range of about 1 ppm to about 500,000 ppm or in the range of about 10 ppm to about 500,000 ppm. A substantially homogeneous magnetic field may include those having a homogeneity measure lower than about 200,000 ppm, preferably lower than about 100,000 ppm, preferably lower than about 50,000 ppm, preferably lower than about 1,000 ppm, preferably lower than about 100 ppm, or preferably lower than 10 ppm. For example, a substantially homogeneous magnetic field may include those having a homogeneity measure of about 200,000 ppm, about 100,000 ppm, about 90,000 ppm (e.g., 88,000 ppm), about 80,000 ppm, about 70,000 ppm, about 60,000 ppm, about 50,000 ppm, about 40,000 ppm, about 30,000 ppm, about 20,000 ppm, about 10,000 ppm, about 5,000 ppm, about 1,000 ppm, about 100 ppm, about 50 ppm, about 10 ppm, or about 1 ppm.

By "signal-to-noise ratio," as used herein, is meant the ratio of the magnitude of a desired signal over the magnitude of background noise, i.e., ratio of signal power to noise power. The signal-to-noise ratio can be determined using methods known in the art, e.g., by applying a fast fourier transform (FFT) to the FID signal and determine the signal-to-noise ratio according to the formula: (maximum amplitude of the FFT)/(standard deviation of the portion of the FFT with noise only)=signal-to-noise ratio. Alternatively, the signal-to-noise ratio can be determined from $T_2$ relaxation curve, e.g., according to the formula: (maximum signal intensity of acquired data)/(root-mean-square noise obtained from an exponential fit)=signal-to-noise ratio, or according to the formula (maximum signal intensity of acquired data)/(standard deviation of the portion of the data with noise only (flat part of a $T_2$ relaxation curve))=signal-to-noise ratio. The signal-to-noise ratio may also be obtained according to the formula (maximum signal intensity)/(standard deviation of the last from 10 to 150 echoes (e.g., 100 echoes))=signal-to-noise ratio.

By "single-voxel spectroscopy," as used herein, is meant an NMR method using a single voxel for data collection.

By "multi-voxel spectroscopy," as used herein, is meant an NMR method using multiple voxels for data collection.

By "relaxation parameter," as used herein, is meant any raw or processed data associated with NMR measurement of relaxation time of hydrogen nuclei in water. The relaxation parameter may be a relaxation time (e.g., a $T_2$ relaxation time, a $T_1$ relaxation time, a $T_{1rho}$ relaxation time, or a $T_2^*$ relaxation time). The relaxation parameter obtained from processed data may include one or more peak height values of a relaxation signal, one or more peak width values of a relaxation signal (e.g., full-width at half maximum (FWHM)), or an area under one or more peaks of a relaxation signal. The relaxation parameter obtained from processed data may be a signal deconvolved into one or more hydrogen nuclei (e.g., hydrogen nuclei of water) compartments or may be a signal that includes the combination of two or more hydrogen nuclei (e.g., hydrogen nuclei of water)compartments.

By "close proximity," as used herein, is meant a point on the surface of a first object (e.g., a tissue portion of a subject) is within 20 cm (e.g., within 10 cm, 5 cm, 2 cm, 1 cm, or 0.5 cm) of a point on the surface of a second object (e.g., a device), provided that these points are the spatially closest points between the two objects. The term "close proximity" may further indicate that a third point on a surface opposing the first point of the first object is within 20 cm (e.g., within 10 cm, 5 cm, 2 cm, 1 cm, or 0.5 cm) of a fourth point on the surface of the second object, provided that the second and fourth points are not the same and that direct lines connecting the first and second points and the third and fourth points do not traverse the first or second object.

By "portable," as used herein, is meant a property of being sufficiently light and small so as to be carried or worn for at least 15 minutes by an average human (e.g., a portable object may have a mass of less than 5 kg, 3 kg, 2 kg, or 1 kg).

DETAILED DESCRIPTION

Figure 1:
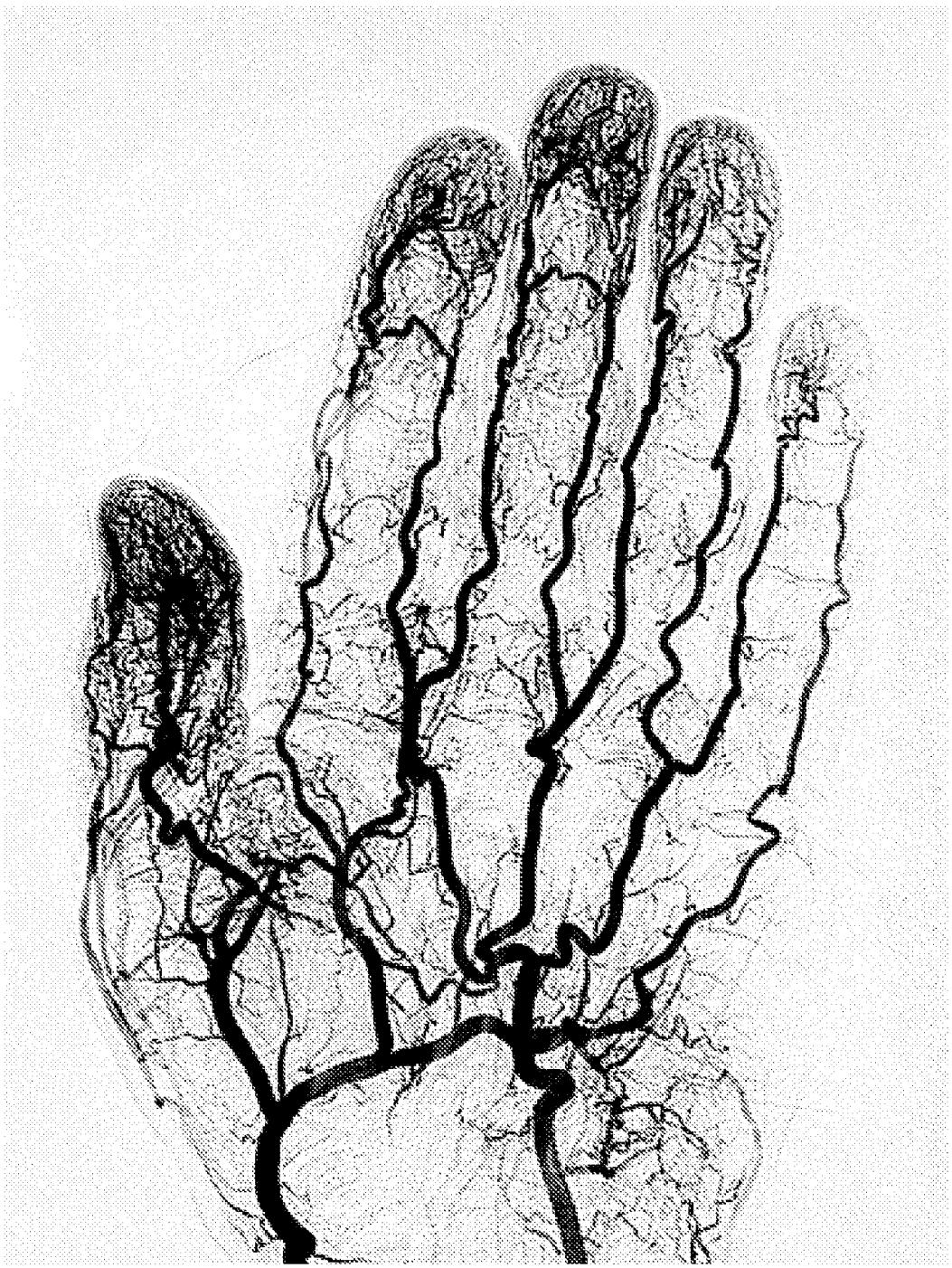
FIG. 1 is an X-ray angiographic image of a hand. The photograph shows the high degree of vascularization of the finger tips. Reproduced from the American Society for Surgery of the Hand; The Cold Hand (http://www.assh.org/Public/HandConditions/Pages/Cold-Hand.aspx).

We have discovered methods and developed NMR capable devices for rapid and non-invasive in vivo determination of hydration state or vascular volume that assess water content in a portion of a tissue of the body of a subject. The invention uses NMR-based sensors and methods to assess water content in the body. We have employed (1) signal processing algorithms to analyze overall hydration changes in the biological sample and (2) algorithms to analyze hydration state of different fluid compartments in the biological sample, and have developed an NMR-sensor that assesses intravascular fluid status non-invasively, the data from the device corresponding to invasive, clinically-accepted measures of the same metric. The results described herein demonstrate that NMR relaxivity measurements can be used to determine physiological hydration state of an animal or patient as a whole. Further, rather than determining the ratio of fat to water, we have surprisingly found that the NMR relaxivity measurement itself can be correlated to the hydration state of the animal or patient, and further that measurements in target tissues (for example, peripheral tissues, such as the finger) are diagnostic of the overall hydration state of the subject. In addition, we have found that relaxivity component analysis can be can be used to determine the amount of water in different compartments of a target tissue. These compartments include the intracellular, interstitial, and vascular spaces of the tissue. We also show that, by targeting the measurement of a specific tissue, the signal for one desired compartment can be maximized. For example, we find that NMR relaxivity measurements of a finger can be used to measure the vascular compartment. The vascular volume is a particularly important measure of hydration state, and we have surprisingly found that a simple relaxation parameter associated with a relaxation time measurement (e.g., $T_2$ measurement) of the finger (or other tissues) correlates with the overall hydration state of a human.

Also surprisingly, we have found that NMR measurements of a given tissue volume of interest, which is less than the whole body of a subject, include relaxation signal from the vascular space. This is surprising since the MRI literature generally describes the absence of vascular signal in measurements and images unless a contrast agent is used (Bonn et al., *Annual Review of Fluid Mechanics*, 40, 209-233, 2008). This is the result of two factors: the relatively small voxel being measured and the speed at which blood is flowing. Proton excitations of the water (vasculature) in the voxel of interest produce no signal as the excited material exits the probed region in a time that is faster than the NMR pulse sequence. One can theoretically measure blood by increasing the volume size and decreasing the flow rate. We have surprisingly found that we can detect signal from the vascular space by increasing the measurement volume and by assaying a region in the body that has reduced blood flow (e.g., small vessels in peripheral tissue). The techniques described herein can be used to assess hydration state and/or vascular volume of the whole subject using, e.g., a tissue volume of less than about 20 $cm^3$, such as about 3.3 $cm^3$.

Figure 2:
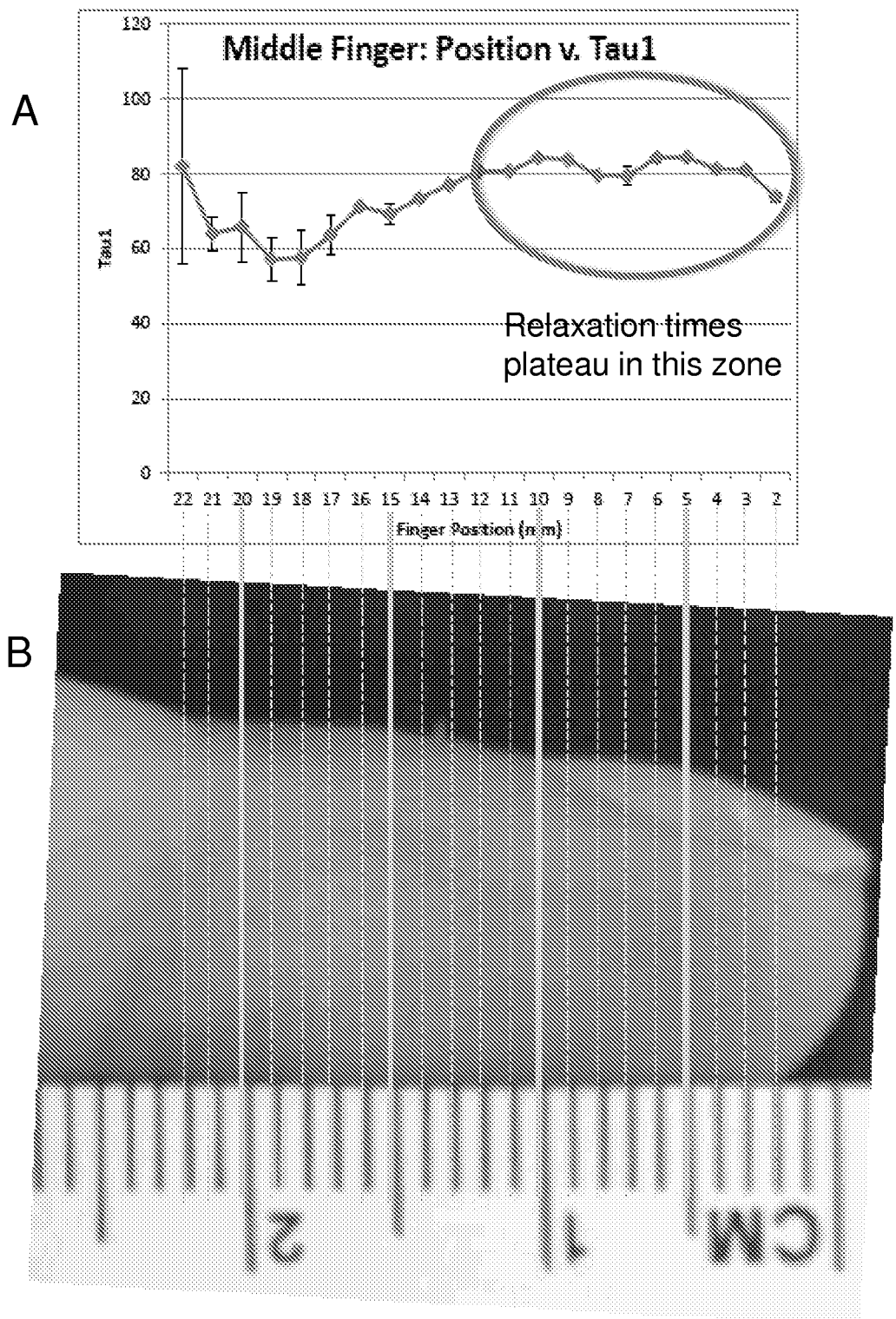
FIG. 2A is a graph comparing the relaxation time (Tau 1 corresponding to $T_2$ relaxation time) of hydrogen nuclei in water within a finger to the location of the water within the finger.
FIG. 2B is a photograph showing a finger portion with lines identifying locations corresponding to those in FIG. 2A.

Vascularization varies with different anatomic locations and tissues of the body. While not limiting the invention to any one tissue, the finger has obvious advantages. The finger contains dense capillary beds with relatively small amounts of muscle mass (see, e.g., FIG. 1). These peripheral capillary networks are where blood velocity is at a minimum (Stucker et al., *Microvascular Research*, 52:188-192, 1996). As mentioned above, a reduced blood velocity is desired to measure the vasculature, such that the excited protons do not exit the field of measurement quickly (see, e.g., FIG. 2). Other peripheral tissues similarly composed of small vessels can be used to assess hydration state and/or vascular volume using the methods and devices described herein. These tissues include, e.g., the cheek, toes, and ears. Finally, the finger is particularly convenient for noninvasive measurements. The size of the instrumentation used to practice methods of the invention can be small, such that it would easy for a patient to comfortably place the instrument on the tissue, e.g., a finger, in the field of measurement. Again, while not limited to the finger, tissues and/or anatomic locations for measurement are preferably similar to the described advantages of measurements of the finger.

A compartment is an anatomical feature or a combination of anatomical features, to which a single peak within a multiexponential distribution in time domain is attributed. There exist several reasons for $^1$H NMR compartmentalization (multiexponential) in physiologic systems. Intrinsic material properties govern NMR properties for a given tissue. These material properties reflect the numerous states and interactions of hydrogen atoms within a given sample/tissue. Such states and interactions include: physically and chemically bound versus free proton states, paramagnetic effects, and proton mobility within and outside of the sample. The differences in NMR parameters between tissues as well as multi-exponentiality within a tissue type are reflective of these variables. Most typically, a compartment is that anatomical feature or combination of features where water hydrogen nuclei can migrate at a rate more rapid than the time scale of the NMR measurement. Such water hydrogen nuclei in such a compartment will all appear to have the same relaxivity.

The measured voxel will typically contain several such compartments. Each compartment has its own NMR relaxivity. Thus, the NMR parameters measured from the entire voxel are a superposition of all those compartments contained in the measurement voxel.

Further reasons for compartmentalization exist from the NMR hardware and pulse sequence parameters. Signal to noise ratio (SNR) is highly hardware dependent and reflects signal fidelity—the higher the better. If the SNR is insufficient, resolution of anatomical features that are near the noise floor into separate compartments becomes challenging. The pulse sequence also plays a role in separating anatomical features into separate compartments. If the time for interaction and exchange of hydrogen between two or more anatomical features is less than that of the applied pulse length and echo time, the anatomical features will not be discernible and appear as a single compartment. For additional discussion of multi-exponential $T_2$ relaxation, see Bertram et al., *J. Agric. Food. Chem.*, 49:3092-3100, 2001, and Kamman et al., *Magn. Reson. Imaging*, 5:381-392, 1987.

Compartmentalization is observed in the NMR data after processing the data into a relaxogram by various deconvolution methods, including an inverse laplace transform (ILT) or non-negative least squares (NNLS) fitting. The relaxation parameters may refer to the amplitudes of, width of, or area under, the peaks of the relaxogram. Furthermore, relaxation parameter may refer to the ratio of amplitudes (i.e. peak heights) or relaxation times between various compartments. Compartments are identified either by a deconvolution method (i.e. generation of a relaxogram) or by multi-exponential fitting methods.

Methods of the Invention

Our technology relies on the discovery that nuclear magnetic resonance (NMR)-relaxivity measurements can be directly correlated with an individual's hydration state and water compartment volume (e.g., vascular volume). NMR is a physical phenomenon in which nuclei of interest are exposed to and interact with applied magnetic fields. The time required for the nuclei to return to equilibrium, after perturbation, is known as the relaxation time and can be broken down into spin-lattice ($T_1$) and spin-spin relaxation ($T_2$) measurements. The state of the nuclei of interest, ranging from a molecular conformation to mobility within a larger aggregate sample, governs $T_1$ and $T_2$ relaxation times. $T_1$ and $T_2$ relaxation times may be measured using NMR experiments and pulse sequences known in the art, e.g., inversion recovery experiment, Carr-Purcell-Meiboom-Gill (CPMG) pulse sequence, Hahn echo decay experiment, pulse field gradient (PFG) sequences, and free induction decay experiment.

We are specifically interested in $^1$H NMR, which detects the relaxivity of hydrogen (in all states). Given that water ($H_2O$) is two-thirds hydrogen, $^1$H NMR is well positioned to detect physiologic water changes. Thus, although water is being measured on a broad scale, water location in various tissues and within different compartments within a tissue will yield differences in measured relaxation rates and signal intensities.

The present invention provides methods for non-invasively determining a hydration state or a vascular volume of a subject (e.g., an animal, such as a human) using a device capable of nuclear magnetic resonance (NMR) measurement. The method involves exposing a portion of a tissue of the subject in vivo to a magnetic field and RF pulse from the device to excite hydrogen nuclei of water within the tissue portion, and measuring a relaxation parameter of the hydrogen nuclei in the tissue portion, the relaxation parameter being a quantitative measure of the hydration state of the subject. The relaxation parameter may be a relaxation time (e.g., $T_2$ relaxation time, $T_1$ relaxation time, a $T_{1,rho}$ relaxation time, or $T_2^*$ relaxation time), a signal intensity (e.g., a height or a width (e.g., FWHM) of a peak corresponding to hydrogen nuclei of water, e.g., in relaxation time domain), or an area under a peak (e.g., a peak corresponding to hydrogen nuclei of water, e.g., in relaxation time domain). We have found that relaxation parameter analysis can be used to determine the amount of water in different compartments of a target tissue. These compartments include the intracellular, extracellular, interstitial, and vascular spaces of the tissue. Thus, the hydration state of an intracellular, interstitial, extracellular, or vascular space of the tissue portion can be measured; preferably, the hydration state of the vascular space is measured; more preferably, the hydration state of the vascular space of a subject having congestive heart failure is measured. The tissue portion may have a reduced blood flow relative to other tissues in the subject. The tissue portion may be a peripheral body part, e.g., a finger, an ear, a nose, a cheek, a toe, a foot, a calf, a hand, a wrist, a leg, or an arm (e.g., a forearm). Preferably, the tissue portion is a finger, an ear, a cheek, or a toe. More preferably, the tissue portion is a finger, even more preferably the tissue portion is a finger tip (see, e.g., FIGS. 1 and 2).

The methods of the invention can be performed on a tissue portion of a subject once or repeated two or more times. The methods of the invention can be performed on a tissue portion of a subject two or more times over a period of time (e.g., months, weeks, days, hours, minutes, or seconds), as necessary to obtain comparative measurements that can be used to detect, e.g., increases or decreases in the relaxation parameter of hydrogen nuclei, which correlate to increases or decreases in water content, respectively. These increases or decreases can be used to assess whether a subject is euhydrated, dehydrated, or overhydrated.

The methods of the invention can be performed on a tissue volume of at least about 0.01 cm$^3$ (e.g., at least about 0.05 cm$^3$, at least about 0.1 cm$^3$, at least about 0.5 cm$^3$, or at least about 1.0 cm$^3$). The methods of the invention can be performed on a tissue portion that is less than the whole of a subject, but that may include a tissue volume of at most about 70,000 cm$^3$ (e.g., at most about 1,000.0 cm$^3$, at most about 20.0 cm$^3$, at most about 10.0 cm$^3$, or at most about 5.0 cm$^3$). The methods of the invention may be performed on a tissue portion that is less than the whole of a subject, but that may include a tissue volume within a range of about 0.01 cm$^3$ to about 70,000 cm$^3$, about 0.05 cm$^3$ to about 70,000 cm$^3$, preferably about 0.1 cm$^3$ to about 70,000 cm$^3$, more preferably about 0.5 cm$^3$ to about 70,000 cm$^3$, and most preferably 1.0 cm$^3$ to about 70,000 cm$^3$. The methods of the invention may be performed on a tissue volume within a range of about 0.01 cm$^3$ to about 20.0 cm$^3$, about 0.05 cm$^3$ to about 20.0 cm$^3$, preferably about 0.1 cm$^3$ to about 20.0 cm$^3$, more preferably about 0.5 cm$^3$ to about 20.0 cm$^3$, and most preferably 1.0 cm$^3$ to about 20.0 cm$^3$. The methods of the invention may be performed on a tissue volume within a range of about 0.01 cm$^3$ to about 10.0 cm$^3$, about 0.05 cm$^3$ to about 10.0 cm$^3$, preferably about 0.1 cm$^3$ to about 10.0 cm$^3$, more preferably about 0.5 cm$^3$ to about 10.0 cm$^3$, and most preferably about 1.0 cm$^3$ to about 10.0 cm$^3$. The methods of the invention may be performed on a tissue volume within a range of about 0.01 cm$^3$ to about 5.0 cm$^3$, about 0.05 cm$^3$ to about 5.0 cm$^3$, preferably about 0.1 cm$^3$ to about 5.0 cm$^3$, more preferably about 0.5 cm$^3$ to about 5.0 cm$^3$, and most preferably about 1.0 cm$^3$ to about 5.0 cm$^3$. The methods of the invention may be performed on a tissue volume within a range of about 0.01 cm$^3$ to about 1.0 cm$^3$, about 0.05 cm$^3$ to about 1.0 cm$^3$, about 1.0 cm$^3$ to about 5.0 cm$^3$, 2.0 cm$^3$ to about 5.0 cm$^3$, about 2.0 cm$^3$ to about 4.0 cm$^3$, about 5.0 cm$^3$ to about 10.0 cm$^3$, about 10.0 cm$^3$ to about 20.0 cm$^3$, or about 20.0 cm$^3$ to about 1,000.0 cm$^3$. The methods of the invention can be performed on a tissue volume of about 3.0 cm$^3$, such as 3.3 cm$^3$.

The methods of invention may include the use of single-voxel spectroscopy (SVS). In such measurements, the entire tissue volume on which the method of the invention is performed is used as a single voxel. Multiple single-voxel measurements may be obtained and used in the methods of the invention to assess hydration state and/or vascular volume of a subject. Alternatively, multi-voxel spectroscopy can be used, in which the tissue volume is divided into multiple voxels.

According to the methods of the invention, the measured signal is a relaxation decay curve. The decay curve may provide a relaxation parameter, such as a $1_2$ relaxation time, a $T_{1rho}$ relaxation time, a $T_2^*$ relaxation time, or a $T_1$ relaxation time. The relaxation parameter may be a measure of signal intensity, such as a height or a width of a peak of a relaxation signal (e.g., FWHM). Alternatively, the relaxation parameter may be a measure of an area under a peak of a relaxation signal. This measured signal may be analyzed using an analytical method that includes, e.g., one or more of data deconvolution, single exponential regression analysis, and/or multi-exponential regression analysis. Preferably, the analytical method is data deconvolution or multi-exponential regression analysis. Data deconvolution can be performed using methods known in the art, e.g., Inverse Laplace Transform (ILT) or Non-negative Least Squares (NNLS) fitting.

The methods of the invention provide for the use of a device that is configured to be in close proximity to the tissue of the subject when used to assess hydration state or vascular volume. For example, a point on the surface of the device may be within about 20 cm (e.g., about 10 cm, about 5 cm, about 2 cm, about 1 cm, or about 0.5 cm) of the closest point on the surface of the tissue portion on which the measurement is being performed. A point on the surface of the device may be substantially in contact with the closest point on the surface of the tissue portion on which the measurement is being performed. Alternatively, a first point on the surface of the device may be within about 20 cm (e.g., about 10 cm, about 5 cm, about 2 cm, about 1 cm, or about 0.5 cm) of a second point on the surface of a tissue portion on which the measurement is being performed, such that the two points are the most proximal points between the device and the tissue portion on which the measurement is being performed. Further, a third point on a surface of the tissue portion opposing the first point may be within about 20 cm (e.g., about 10 cm, about 5 cm, about 2 cm, about 1 cm, or about 0.5 cm) of a fourth point on the surface of a device, such that the third and fourth points are the most proximal points between the device and the tissue portion on which the measurement is being performed. In certain examples, these requirements are met under the condition that none of the straight lines connecting the first and second points and the third and fourth points traverse the body of the device or the tissue portion on which the measurement is being performed. According to the methods of the invention, the device can be portable (e.g., hand-held, wearable, or even attached to the tissue portion). The device may also be a bench-top device (e.g., a portable bench-top device).

The hydration state or a vascular volume of a tissue of a subject can be determined according to the methods of the invention using a device that is configured to provide a substantially homogeneous magnetic field over a volume of at least about 0.01 cm$^3$ (e.g., at least about 0.05 cm$^3$, at least about 0.1 cm$^3$, at least about 0.5 cm$^3$, or at least about 1.0 cm$^3$). According to the methods of the invention, the hydration state or a vascular volume of a tissue of a subject can be determined using a device that is configured to provide a substantially homogeneous magnetic field over a volume of at most about 70,000 cm$^3$ (e.g., at most about 1,000.0 cm$^3$, at most about 20.0 cm$^3$, at most about 10.0 cm$^3$, or at most about 5.0 cm$^3$). According to the methods of the invention, the device may be configured to provide a substantially homogeneous magnetic field over a volume within a range between about 0.01 cm$^3$ and about 70,000 cm$^3$, preferably between about 0.05 cm$^3$ and about 70,000 cm$^3$, preferably between about 0.1 cm$^3$ and about 70,000 cm$^3$, preferably between about 0.5 cm$^3$ and about 70,000 cm$^3$, or preferably between about 1.0 and 70,000 cm$^3$. According to the methods of the invention, the device may be configured to provide a substantially homogeneous magnetic field over a volume within a range between about 0.01 cm$^3$ and about 1,000 cm$^3$, preferably between about 0.05 cm$^3$ and about 1,000 cm$^3$, preferably between about 0.1 cm$^3$ and about 1,000 cm$^3$, preferably between about 0.5 cm$^3$ and about 1,000 cm$^3$, or preferably between about 1.0 and about 1,000 cm$^3$. According to the methods of the invention, the device may be configured to provide a substantially homogeneous magnetic field over a volume within a range between about 0.01 cm$^3$ and about 20.0 cm$^3$, about 0.05 cm$^3$ and about 20.0 cm$^3$, preferably between about 0.1 cm$^3$ and about 20.0 cm$^3$, preferably between about 0.5 cm$^3$ and about 20.0 cm$^3$, or preferably between about 1.0 cm$^3$ and about 20.0 cm$^3$. According to the methods of the invention, the device may be configured to provide a substantially homogeneous magnetic field over a volume within a range between about 0.01 cm$^3$ and about 10.0 cm$^3$, about 0.05 cm$^3$ and about 10.0 cm$^3$, preferably between about 0.1 cm$^3$ and about 10.0 cm$^3$, preferably between about 0.5 cm$^3$ and about 10.0 cm$^3$, or preferably between about 1.0 cm$^3$ and about 10.0 cm$^3$. According to the methods of the invention, the device may be configured to provide a substantially homogeneous magnetic field over a volume within a range between about 0.01 cm$^3$ and about 5.0 cm$^3$, about 0.05 cm$^3$ and about 5.0 cm$^3$, preferably between about 0.1 cm$^3$ and about 5.0 cm$^3$, preferably between about 0.5 cm$^3$ and about 5.0 cm$^3$, or preferably between about 1.0 cm$^3$ and about 5.0 cm$^3$. According to the methods of the invention, the device may be configured to provide a substantially homogeneous magnetic field over a volume within a range between about 0.01 cm$^3$ and about 1.0 cm$^3$, about 0.05 cm$^3$ and about 1.0 cm$^3$, 1.0 cm$^3$ and about 5.0 cm$^3$, about 2.0 cm$^3$ and about 5.0 cm$^3$, about 2.0 cm$^3$ and about 4.0 cm$^3$, about 5.0 cm$^3$ and about 10.0 cm$^3$, about 10.0 cm$^3$ and about 20.0 cm$^3$, or about 20.0 cm$^3$ and about 1,000.0 cm$^3$. According to the methods of the invention, the hydration state or a vascular volume of a tissue of a subject can be determined using a device that is configured to provide a substantially homogeneous magnetic field over a volume of about 3.0 cm$^3$, such as 3.3 cm$^3$. The device may be configured to provide a substantially homogeneous magnetic field over a tissue volume on which a measurement according to the methods of the invention is performed.

According to the methods of the invention, the hydration state or a vascular volume of a tissue of a subject can be determined using a device that is configured to provide a signal-to-noise ratio of greater than about 5 (e.g., preferably greater than about 10, more preferably greater than about 20, even more preferably greater than about 50 (e.g., between about 50 and about 60, such as 53), or even more preferably greater than about 100) from a measurement over a volume of at least about 0.01 cm$^3$ (e.g., at least about 0.05 cm$^3$, at least about 0.1 cm$^3$, at least about 0.5 cm$^3$, or at least about 1.0 cm$^3$). According to the methods of the invention, the hydration state or a vascular volume of a tissue of a subject can be determined using a device that is configured to provide a signal-to-noise ratio of greater than about 5 (e.g., preferably greater than about 10, more preferably greater than about 20, even more preferably greater than about 50 (e.g., between about 50 and about 60, such as 53), or even more preferably greater than about 100) from a measurement over a volume of at most about 70,000 cm$^3$ (e.g., at most about 20.0 cm$^3$, at most about 10.0 cm$^3$, at most about 5.0 cm$^3$). According to the methods of the invention, the hydration state or a vascular volume of a tissue of a subject can be determined using a device that is configured to provide a signal-to-noise ratio of greater than about about 5 (e.g., preferably greater than about 10, more preferably greater than about 20, even more preferably greater than about 50 (e.g., between about 50 and about 60, such as 53), or even more preferably greater than about 100) from a measurement over a volume of about 3.0 cm$^3$, such as 3.3 cm$^3$. The device may be configured to provide a signal-to-noise ratio of greater than about 5 (e.g., preferably greater than about 10, more preferably greater than about 20, even more preferably greater than about 50 (e.g., between about 50 and about 60, such as 53), or even more preferably greater than about 100) from a measurement over a tissue volume on which a measurement according to the methods of the invention is performed.

According to the methods of the invention, the hydration state of a subject can be determined by obtaining one or more relaxation parameter measurements and comparing the measured relaxation parameter to a reference measurement. The reference measurement can be one or more earlier measurements on the tissue portion (e.g., substantially the same tissue portion) of the subject, or can be a measurement on a tissue portion of a population of subjects having a known hydration state (e.g., euhydration, hyponatremia, or hypernatremia). When the relaxation parameter is a relaxation time, an increase in relaxation time relative to the reference measurement indicates an increased hydration level of the subject. Alternatively, a decreased relaxation time relative to the reference measurement indicates a decreased hydration level of the subject. When the relaxation parameter is a measure of the intensity of the peak (e.g., height of the peak and/or width of the peak) of a relaxation signal, an increase in peak intensity relative to the reference measurement indicates an increased hydration level of the subject (e.g., an overhydration relative to prior euhydration or an overhydration relative to euhydration state of a population of reference subjects), and a decrease in peak intensity relative to the reference measurement indicates a decreased hydration level of the subject (e.g., a dehydration relative to prior euhydration or a dehydration relative to euhydration state of a population of reference subjects). When the relaxation parameter is a measure of the area under the peak of a relaxation signal, an increase in peak area relative to the reference measurement indicates an increased hydration level of the subject (e.g., an overhydration relative to prior euhydration or a dehydration relative to euhydration state of a population of reference subjects), and a decrease in peak area relative to the reference measurement indicates a decreased hydration level of the subject (e.g., a dehydration relative to prior euhydration or a dehydration relative to euhydration state of a population of reference subjects).

A reference hydration state of a subject may also be established using other methods known in the art, e.g., plasma osmolality measurements, urine osmolality measurements, urine specific gravity measurements, total body water measurements, or combinations thereof. Once a reference baseline for a subject indicative of the hydration state of the subject (e.g., dehydration, euhydration, or overhydration) is established, methods of the invention may then be used for rapid and non-invasive assessment of changes in the hydration state of the subject over time. For examples of methods for assessment of a hydration state see Kenefick et al., (*Wilderness Medicine Textbook,* Chapter 70, pp. 71-82 and pp. e70-1-e70-4, 2012; this reference is incorporated herein in its entirety by reference).

The methods of the invention also include assessing the state of the vascular volume of a subject as a whole by measuring the vascular volume, or changes in vascular volume, in a portion of a tissue of the subject (i.e., less than the whole subject). The vascular volume of a tissue portion of a subject can be determined by obtaining one or more relaxation parameter measurements and comparing a measured relaxation parameter to a reference measurement. The reference measurement can be one or more earlier measurements on the tissue portion (e.g., substantially the same tissue portion) of the subject, or can be a measurement on a tissue portion of a population of subjects having a known vascular volume. When the relaxation parameter is a relaxation time, an increase in relaxation time relative to the reference measurement indicates an increased vascular volume of the subject, and a decreased relaxation time relative to the reference measurement indicates a decreased vascular volume of the subject. When the relaxation parameter is a measure of the intensity of the peak (e.g., height of the peak and/or width of the peak) of a relaxation signal, an increase in peak intensity relative to the reference measurement indicates an increased vascular volume of the subject, and a decrease in peak intensity relative to the reference measurement indicates a decreased vascular volume of the subject. When the relaxation parameter is a measure of the area under the peak of a relaxation signal, an increase in peak area relative to the reference measurement indicates an increased vascular volume of the subject, and a decrease in peak area relative to the reference measurement indicates a decreased vascular volume of the subject.

The methods of the invention can be used to determine whether a subject (e.g., a human) has or is at risk of having a hydration imbalance by assessing the hydration state and/or vascular volume of the subject. A subject may be an elderly subject, a child, an athlete, military personnel (e.g., a soldier), an aircraft pilot, an air traffic controller, a locomotive engineer, or a crane operator. A subject may have a disease or condition that increases the risk of having or results from a hydration imbalance. Such diseases or conditions may be, e.g., congestive heart failure (CHF), renal failure, liver cirrhosis, nephrotic syndrome, brain swelling, diabetes, staphylococcal infection, nephrolithiasis, diarrhea, colitis, preferably ulcerative colitis, pyelonephritis, cystic fibrosis, Huntington's disease, rotavirus infection, herpangina, salmonellosis, norovirus infection, pertussis, cryptosporidium infection, cholera, coma, or water intoxication. The hydration imbalance that may be detected using the methods of the invention can be hyponatremia or hypernatremia. Other hydration imbalances, such as hypokalemia or hyperkalemia, can be detected using the methods of the invention. The detection of changes in the hydration state or vascular volume of the subject (e.g., a decrease in water content indicative of dehydration or an increase in water content indicative of water intoxication) may indicate the need for therapeutic intervention (described in detail below).

The methods of the invention can be performed using a device that includes (a) one or more magnets, (b) an RLC circuit, and (c) a processor, where the processor is capable of (i) determining a relaxation parameter of the hydrogen nuclei and (ii) comparing the determined relaxation parameter to a reference value of the parameter in order to assess the hydration state or vascular volume of a subject.

The methods of the invention can be performed using a device that includes a processor capable of analyzing data from single-voxel spectroscopy (SVS) or multi-voxel spectroscopy. Multi-voxel spectroscopy may utilize two or more voxels of the same or different volume. According to the methods of the present invention, the processor may compare several single-voxel measurements to assess changes between measurements that can be used to indicate the hydration state and/or vascular volume of the subject, e.g., an increase in relaxation time between two or more SVS measurements indicates an increased vascular volume and/or rehydration of the subject, whereas a decrease indicates a decrease in vascular volume and/or dehydration of the subject. The processor may instead compare several multi-voxel measurements to assess changes between measurements that can be used to indicate the hydration state and/or vascular volume of the subject, e.g., an increase in relaxation time between two or more multi-voxel measurements indicates an increased vascular volume and/or rehydration of the subject, whereas a decrease indicates a decrease in vascular volume and/or dehydration of the subject. Alternatively, the processor may compare a combination of single-voxel and multi-voxel measurements to assess changes between measurements that can be used to indicate the hydration state and/or vascular volume of the subject.

The methods of the invention described herein can be performed on a subject to determine the changes in the hydration state or vascular volume of the subject over time. For example, the measurements described herein can be performed on the subject two or more times over a period of 1 or more hours (e.g., days, weeks, or months).

As a non-limiting example, the methods of the invention may include determining and maintaining hydration state of subject, such as a subject suffering from, or suspected of having, congestion. In this example, the subject wears the device of the invention, e.g., affixed to the finger tip. The device performs measurements one or more times over a period of time (e.g., one or more times every 30 minutes) according to the methods of the invention. The device includes a sensor (e.g., an RLC circuit) that detects relaxation parameter data and sends the data to a processor (e.g., a processor in a computer containing a computer readable storage medium), which receives and processes the data. The processor can then convert the data into a measure of the hydration state of the subject. The device outputs the state of the hydration state to the subject or medical personnel in a signal (e.g., in a visual, auditory, tactile (e.g., vibratory), or other signal) that notifies the subject or medical personnel of their state. If the device indicates that subject is dehydrated, the subject can then take appropriate actions to rehydrate or medical personnel can take appropriate actions to rehydrate the subject, e.g., as described herein.

The methods of the invention can be used to determine a volume of any water compartment, such as an intracellular, an interstitial, or an extracellular compartment. Thus, methods of the invention directed to determining a vascular volume may also be used to determine an intracellular volume, an interstitial volume, or an extracellular volume of a water compartment other than a vascular volume.

Certain individual parameters may be used in the methods of the invention to adjust the measured data for the purposes of data homogenization across populations of subjects. Such parameters can include a finger size, body mass index (height and weight), finger temperature, or gender, or a combination thereof. Several of these parameters can affect NMR measurements for the following reasons: 1) NMR signal amplitude correlates with the amount and proton density of sample being measured, thus, finger size, gender, and BMI have the potential to influence this, 2) physical effects of temperature on the finger can cause vasodilation or contraction which can conceivably effect the NMR signal, and 3) variation in sample temperature has the potential to affect the relaxation time. The NMR measurement output, e.g., signal amplitude, can be normalized by dividing the output value by the parameter or a combination of the parameters, provided that the parameter(s) influence the NMR measurement.

The methods of the invention may also be used to measure physiological parameters (e.g., blood parameters) other than hydration state or vascular volume. For example, the methods of the invention may be used to identify a subject as suffering from hemodilution or to determine the hematocrit concentration, or blood oxygenation. In the methods of determining hematocrit concentration or blood oxygenation levels, the decrease in the relaxation parameter (e.g., $T_1$ relaxation time or $T_2$ relaxation time) relative to the reference measurement would be indicative of an increase in the hematocrit concentration or a decrease in blood oxygenation. In the methods of identifying a subject as suffering from hemodilution, an increase in relaxation parameter (e.g., $T_1$ relaxation time or $T_2$ relaxation time) relative to the reference measurement would be indicative of the hemodilution.

The methods of the invention can be performed using any of the exemplary devices of the invention described in detail below.

Methods of Treatment

The methods of the invention may also include treating a subject in need thereof once the need has been detected following performance of the diagnostic methods of the invention, as discussed above. The methods for determining hydration state and/or vascular volume of a subject, discussed above, can be performed one or more times, as needed, to assess the hydration state (euhydration, dehydration, or water intoxication) of a subject or their vascular volume. Once a hydration imbalance has been detected, the methods of the invention may further include treating the subject if the subject is identified as having a hydration imbalance.

A subject determined to be dehydrated may be treated to control the route by which fluids are lost, e.g., by administering medication or changing an environment to reduce diarrhea, vomiting, or transcutaneous losses. Alternatively or in combination with the aforementioned therapy, the subject may treated by oral rehydration therapy or fluid replacement by, e.g., intravenous or subcutaneous therapy. Oral rehydration therapy may include administering an aqueous solution orally (e.g., water or water containing electrolytes). Oral rehydration therapy (ORT) is 95% effective in cases of mild to moderate dehydration and can be easily performed outside the hospital. It is used with individuals who are able to drink and do not have significant mental or physical compromise. ORT is less invasive, less expensive, and associated with less morbidity than other rehydration methods. For a discussion of oral rehydration therapy, see N.G.C. (n.d.), "Oral Rehydration Therapy (ORT) in Children," Agency for Healthcare Research and Quality (AHRQ), Rockville, Md., at http://www.guideline.gov/content.aspx?id-38900; and Thomas et al., *J. Am. Med. Dir. Assoc.,* 9:292-301, 2008. Fluid replacement therapy includes administering an aqueous solution intravenously or subcutaneously (e.g., saline). Subcutaneous infusions do not require hospitalization and are suitable for home care since minimal training is required for safely starting and maintaining the infusion. The most common adverse effect is mild subcutaneous edema. Approximately 3 L can be delivered in a 24-hour period at two separate infusion sites (Sasson and Shvartzman, *Hypodermoclysis,* 8-10, 2001). Intraveneous (IV) fluid replacement is the standard of care in cases of severe dehydration. It typically requires hospitalization and trained medical personnel to start and maintain the infusion. IV therapy allows greater volumes of fluid to be delivered as well as faster uptake than any other method. Improper monitoring of IV fluid therapy can lead to fluid overload, however, which may be life threatening (Thomas et al., *J. Am. Med. Dir. Assoc.,* 9:292-301, 2008).

A subject determined to be overhydrated (e.g., suffering from congestion) may be treated by administering a diuretic (e.g., thiazide or mannitol), a beta-blocker, an angiotensin-converting enzyme (ACE) inhibitor (e.g., captopril), or a vasopressin receptor antagonist (e.g., conivaptan, lixivaptan, or satavaptan), or a combination thereof. The therapies are life-saving but have undesired side effects that lead to increased morbidity and mortality. Thus, early management of overhydration, in particular, congestion, would allow for the use of lower doses of medication (De Luca et al., *Reviews in Cardiovascular Medicine,* 7:69-74, 2006). Current approach to dosing is conservative introduction of medication with subsequent adjustment based on symptoms (Davies et al., *Management: diuretics, ACE inhibitors, and nitrates,* 320:3-6, 2000). Another treatment of overhydration (e.g., congestion) may be ultrafiltration, which involves the mechanical removal of fluid from the blood stream. This method requires volume status assessment; however, current methods for volume status assessment including biochemical markers, bioimpedance, and blood volume monitoring are incapable of accurately guiding ultrafiltration. The frequently used approach for dosing ultrafiltration therapy is to estimate fluid excess by comparing the patient's current weight with their baseline weight and remove at least 50-60% of that weight without causing hemodynamic instability or worsening renal function (see, e.g., Costanzo and Jessup, *Heart Failure Reviews,* 17:313-24, 2012). A limitation of this approach is that it requires knowing the patient's baseline weight, which is often unavailable. Accordingly, the methods of the invention can be used for dosing ultrafiltration, e.g., by assessing the hydration state of a subject multiple times during the course of the procedure.

Administration of an appropriate therapy to the subject may be triggered automatically by connecting any of the described devices of the invention to a computer which is also connected to a device that is capable of dispensing the above-described therapies or any other appropriate treatment and that dispenses the therapy when the need is indicated. Alternatively, administration of an appropriate therapy may include self-administration or administration by qualified medical personnel.

The subject undergoing treatment for hydration imbalance may be monitored using the methods described herein to prevent overdosing the treatment. The rate of measurements included in the methods of the invention allows quick monitoring of the subject and provides sufficient time for a response (e.g., adjustment of the treatment) to the changes in the hydration state of the subject.

Devices of the Invention

The present invention provides devices configured for measurement of a relaxation parameter of hydrogen nuclei of water in a tissue portion of a subject for assessing a hydration state or a vascular volume of the subject.

The device of the invention may be configured for measurement of a hydration state of a subject using nuclear magnetic resonance (NMR) by performing an NMR measurement of a signal corresponding to a relaxation parameter of hydrogen nuclei in water in a tissue portion of the subject. The device may include: (a) one or more magnets, (b) an RLC circuit, and (c) a processor. The device may be configured to provide a substantially homogeneous magnetic field over a tissue volume of at least about 0.01 cm$^3$ (e.g., a substantially homogeneous magnetic field over a tissue volume in the range of about 0.01 cm$^3$ to about 70,000 cm$^3$, and points therebetween).

The device of the invention may be configured for measurement of a vascular volume of a subject using nuclear magnetic resonance (NMR) by performing an NMR measurement of a signal corresponding to a relaxation parameter of hydrogen nuclei in water in a tissue portion of the subject. The device may include: (a) one or more magnets, (b) an RLC circuit, and (c) a processor. The device may be configured to provide a substantially homogeneous magnetic field over a volume of at least about 0.01 cm$^3$ (e.g., a substantially homogeneous magnetic field over a tissue volume in the range of about 0.01 cm$^3$ to about 70,000 cm$^3$, and points therebetween).

The device of the invention may be configured for measurement of a hydration state or a vascular volume of a subject using nuclear magnetic resonance (NMR) by performing n NMR measurement of a signal corresponding to a relaxation parameter of hydrogen nuclei in water in a tissue portion of the subject. The device may include: (a) an RLC circuit and (b) a processor, and may utilize the magnetic field of the Earth for NMR measurements.

The relaxation parameter may be a relaxation time (e.g., $T_2$ relaxation time, $T_1$ relaxation time, a $T_{1rho}$ relaxation time, or $T_2^*$ relaxation time), a signal intensity (e.g., a measure of peak height and/or width of a relaxation signal from hydrogen nuclei (e.g., hydrogen nuclei of water), e.g., in relaxation time domain), or an area under a peak (e.g., a measure of the area under a peak of a relaxation signal from hydrogen nuclei (e.g., hydrogen nuclei of water), e.g., in relaxation time domain). Relaxation time is measured using NMR. The device is capable of performing an NMR measurement of relaxation time using e.g., $T_2$ relaxation time, $T_2^*$ relaxation time, a $T_{1rho}$ relaxation time, or $T_1$ relaxation time. The device may include one or more magnets, an RLC circuit, and a processor. The device may be configured to provide a substantially homogeneous magnetic field over a tissue volume of at least about 0.01 $cm^3$ (e.g., at least about 0.05 $cm^3$, at least about 0.1 $cm^3$, at least about 0.5 $cm^3$, or at least about 1.0 $cm^3$). The device may be configured to provide a substantially homogeneous magnetic field over a tissue volume of at most about 20.0 $cm^3$ (e.g., at most about 10.0 $cm^3$, or at most about 5.0 $cm^3$). The device may be configured to provide a substantially homogeneous magnetic field over a tissue volume within a range between about 0.01 $cm^3$ and about 20.0 $cm^3$, preferably between about 0.05 $cm^3$ and about 20.0 $cm^3$, preferably between about 0.1 $cm^3$ and about 20.0 $cm^3$, preferably between about 0.5 $cm^3$ and about 20.0 $cm^3$, or even preferably between about 1.0 $cm^3$ and about 20.0 $cm^3$. The device may be configured to provide a substantially homogeneous magnetic field over a tissue volume within a range between about 0.01 $cm^3$ and about 10.0 $cm^3$, preferably between about 0.05 $cm^3$ and about 10.0 $cm^3$, preferably between about 0.1 $cm^3$ and about 10.0 $cm^3$, preferably between about 0.5 $cm^3$ and about 10.0 $cm^3$, or preferably between about 1.0 $cm^3$ and about 10.0 $cm^3$. The device may be configured to provide a substantially homogeneous magnetic field over a tissue volume within a range between about 0.01 $cm^3$ and about 5.0 $cm^3$, preferably between about 0.05 $cm^3$ and about 5.0 $cm^3$, preferably between about 0.1 $cm^3$ and about 5.0 $cm^3$, preferably between about 0.5 $cm^3$ and about 5.0 $cm^3$, or preferably between about 1.0 $cm^3$ and about 5.0 $cm^3$. The device may be configured to provide a substantially homogeneous magnetic field over a tissue volume within a range between about 0.01 $cm^3$ and about 1.0 $cm^3$, about 0.05 $cm^3$ and about 1.0 $cm^3$, about 1.0 $cm^3$ and about 5.0 $cm^3$, about 2.0 $cm^3$ and about 5.0 $cm^3$, about 2.0 $cm^3$ and about 4.0 $cm^3$, about 5.0 $cm^3$ and about 10.0 $cm^3$, or about 10.0 $cm^3$ and about 20.0 $cm^3$. The device may be configured to provide a substantially homogeneous magnetic field over a tissue volume of about 3.0 $cm^3$, such as 3.3 $cm^3$.

The device of the invention may be configured to provide a signal-to-noise ratio greater than about 5 (e.g., greater than about 10, e.g., greater than about 20, greater than about 50 (e.g., between about 50 and about 60, such as 53), or greater than about 100) from measurement on a tissue volume of at least about 0.01 $cm^3$ (e.g., about 0.05 $cm^3$, about 0.1 $cm^3$, at least about 0.5 $cm^3$ or at least about 1.0 $cm^3$). The device may be configured to provide signal-to-noise ratio greater than about 5 (e.g., greater than about 10, greater than about 20, greater than about 50 (e.g., between about 50 and about 60, such as 53), or greater than about 100) from measurement on a tissue volume of at most 20.0 $cm^3$ (e.g., at most 10.0 $cm^3$, at most 5.0 $cm^3$). The device may be configured to provide signal-to-noise ratio greater than about 5 (e.g., greater than about 10, greater than about 20, greater than about 50 (e.g., between about 50 and about 60, such as 53), or greater than about 100) from measurement on a tissue volume of about 3.0 $cm^3$, such as 3.3 $cm^3$.

The device may be configured for measurement of a relaxation parameter of hydrogen nuclei in water in a tissue portion of a subject, where the tissue portion is a peripheral body part. The tissue portion may be located within, e.g., a finger, an ear, a nose, a cheek, a toe, a foot, a calf, a hand, a wrist, a leg, or an arm (e.g., a forearm), or any combination thereof.

The processor of any of the devices of the invention may not be physically incorporated into a body of the device containing one or more magnets and an RLC circuit. Instead, a link between the processor and the rest of the device containing one or more magnets and an RLC circuit may be established using, e.g., any wired system (e.g., any system using TCP/IP set of communication protocols) or any wireless system (e.g., BlueTooth, WiFi, a system employing RF signals, or a system described in, e.g., U.S. Pat. No. 8,457,798, which is incorporated herein by reference in its entirety).

The processor of any of the devices of the invention is capable of quantifying the hydration state or the vascular volume of the subject, e.g., by converting data corresponding to the relaxation parameter of hydrogen nuclei in water in the portion of the tissue of the subject into a measure corresponding to the hydration state or the vascular volume of the subject. The processor may use one or more algorithms to assess hydration state and vascular volume. For example, the algorithm may involve a data deconvolution (e.g., Inverse Laplace Transform (ILT) or Non-negative least squares (NLS) fitting). The data deconvolution provides a relaxogram having the data resolved as a function of relaxation time and signal intensity. The processor may also be capable of converting the relaxation parameter of hydrogen nuclei in water in the portion of the tissue of the subject analyzed into a measure of the hydration state or the vascular volume of the subject through a single-exponential regression analysis. The processor may also be capable of converting the relaxation parameter of hydrogen nuclei in water in the portion of the tissue of the subject analyzed into the measure of the hydration state or the vascular volume of the subject through a multi-exponential regression analysis.

The processor of any of the devices of the invention may be configured to analyze data from single-voxel spectroscopy (SVS) or multi-voxel spectroscopy. Multi-voxel spectroscopy may utilize two or more voxels of the same or different volume. The processor may compare several single-voxel measurements to assess changes between measurements that can be used to indicate the hydration state of the subject, e.g., an increase in relaxation time between two or more SVS measurements indicates an increased vascular volume and/or rehydration of the subject, whereas a decrease indicates a decrease in vascular volume and/or dehydration of the subject.

The devices of the invention may be configured to be in close proximity to the tissue of the subject when used to assess hydration state or vascular volume. For example, a point on the surface of the device may be within about 20 cm (e.g., about 10 cm, about 5 cm, about 2 cm, about 1 cm, or about 0.5 cm) of the closest point on the surface of the tissue portion on which the measurement is being performed. A point on the surface of the device may be substantially in contact with the closest point on the surface of the tissue portion on which the measurement is being performed. Alternatively, a first point on the surface of the device may be within about 20 cm (e.g., about 10 cm, about 5 cm, about 2 cm, about 1 cm, or about 0.5 cm) of a second point on the surface of a tissue portion on which the measurement is being performed, such that the two points are the most proximal points between the device and the tissue portion on which the measurement is being performed. Further, a third point on a surface of the tissue portion opposing the first point may be within about 20 cm (e.g., about 10 cm, about 5 cm, about 2 cm, about 1 cm, or about 0.5 cm) of a fourth point on the surface of a device, such that the third and fourth points are the most proximal points between the device and the tissue portion on which the measurement is being performed. In this example, these requirements can be met under a condition that none of straight lines connecting the first and second points and the third and fourth points traverses the body of the device or the tissue portion on which the measurement is being performed. The device of the invention may be portable (e.g., hand-held, wearable, or even attached to the tissue portion). The device of the invention may be a bench-top device (e.g., a portable bench-top device). The device may be affixed to a subject using, e.g., one or more or straps, bands, clips, Velcro® or other known options. The device may also be wearable on the tissue portion similar to a finger pulse-oximeter (see, e.g., WO 2012/140559, which is incorporated herein by reference).

The devices of the invention include, e.g., an RLC circuit containing an inductor wire, which may be wrapped around a cylindrical element. The cylindrical element may be made using materials known in the art, including, e.g., an acetal copolymer, PTFE, PCTFE, ABS, Polycarbonate, PEEK, glass, and ceramics, and combinations thereof. The inductor wire may be made of a metal, e.g., aluminum, copper, silver, and their alloys. The inductor wire may be cylindrically enclosed within a non-conducting material. The width of the inductor wire may be in the range of 16 to 48 AWG (e.g., 32 AWG). In a non-limiting example, the inductor wire may be an insulated 32 AWG copper wire with a thirteen-turn inductor wrapped around an acetal copolymer cylindrical element.

The device may include one or more magnets (e.g., 1-200 magnets, 2-200 magnets, 2-100 magnets, and 2-50 magnets, e.g., 72 magnets). The magnets are independently selected from a permanent magnet, an electromagnet, and a pulsed electromagnet. The permanent magnets may have any shape known in the art (e.g., cuboidal, spherical, cylindrical, polygonal, or irregular). The permanent magnets may contain a rare earth metal alloy, such as a Nd alloy, preferably a NdFeB alloy (e.g., N52 grade NdFeB alloy). The permanent magnet may contain a Sm alloy, such as a SmCo alloy (e.g., SmCoFeCuZr alloy). Within the device of the invention magnets may be arranged in a cylindrical or a polygonal shape. The magnets may be arranged to produce a central region having a substantially homogeneous magnetic field. For example, the magnets may be arranged in a Halbach array. One or more electromagnets employed in the devices of the invention may be a Helmholtz coil, Maxwell coil, or a solenoid coil. The magnets within the device of the invention may generate a magnetic field with a strength that is at least about 0.01 T (e.g., at least about 0.1 T or at least about 0.2 T). The magnets within the device of the invention may generate a magnetic field of strength that is at most about 2 T (e.g., at most about 1 T, at most about 0.7 T, or at most about 0.5 T). The magnets may generate a magnetic field of strength within a range of about 0.01 T and about 2 T, preferably about 0.05 T to about 1 T, and more preferably about 0.1 T to about 0.7 T (e.g., from about 0.1 T to about 0.5 T). The magnets may generate a magnetic field of strength from about 0.1 T to about 2 T, preferably from about 0.2 T to 2 T, and more preferably from about 0.4 T to about 2 T). The magnetic field strength, as described herein, refers to the magnetic field strength in the portion of the space, where the magnetic field is substantially homogeneous.

The magnets are held by one or more fixtures within the device of the invention. The fixtures may be made of a non-magnetic or a minimally magnetic metal, a non-magnetic or minimally magnetic alloy, a non-metal material, or combinations thereof. A non-metal material can be an acetal copolymer, PTFE, PCTFE, ABS, Polycarbonate, PEEK, polypropylene, polystyrene, or a blend of one or more of these polymers. The fixtures may contain mechanical shims, the adjustment of which allows for control of magnetic field homogeneity. The mechanical shims are adjustable using, e.g., screws embedded in the fixtures or other mechanical means known in the art.

The device of the invention may also contain a temperature control system. The temperature control system may ensure temperature stability of a tissue portion, thereby ascertaining that the hydrogen nuclei of water molecules in the tissue portion absorb an RF pulse at substantially similar chemical shift. The temperature control system can be a closed-loop system. Furthermore, by maintaining magnets of the device at a constant temperature, the temperature control system may help maintaining constant strength and substantial homogeneity of the magnetic field. The temperature control system may contain one or more temperature control elements and one or more electronic elements for thermal control. The temperature control elements may be encased within one or more fixtures of the device. A temperature control element may be a heating element or a cooling element or combination thereof. Heating elements are well known in the art and include any element capable of Joule heating. A heating element converts electricity into heat upon application of electric current. Typical heating elements are made of Nichrome 80/20 (80% nickel, 20% chromium alloy), Kanthal (FeCrAl alloy), or Cupronickel (CuNi alloy). A heating element may be arranged in the shape of, e.g., a wire, a ribbon, a strip, or a coil. A heating element may be coated to prevent oxidation of an alloy. A heating element may be a Peltier module (e.g., U.S. Pat. No. 6,067,802, which is incorporated herein by reference in its entirety). A coating material may be any material impenetrable to oxygen, e.g., chromium oxide, alumina ($Al_2O_3$), ceramics (MgO and $Al_2O_3$). Other heating elements may include a power resistor, a hot plate, an exothermic reaction, or a combination thereof or with any of the above-described heating elements. A cooling element may be incorporated in the devices of the invention including electromagnets so as to ensure that the temperature is maintained within an acceptable range (e.g., 30° C.-40° C.). A cooling element may be any element capable of cooling the medium that this element contacts. A cooling element may be a Peltier module; a non-limiting example of a Peltier module is provided in, e.g., U.S. Pat. No. 7,026,712, which is incorporated herein by reference in its entirety (also, see U.S. Pat. No. 6,067,802). Other cooling elements may include a heatsink (e.g., a metal block (e.g., made of a head-conductive material, such as copper or silver) optionally having one or more fins made of, e.g., copper, or any other heat-conductive metal), a fan-based convection system, or a combination thereof. Other temperature control elements that may be used in the device of the invention include a mobile medium (e.g., water) that upon contact with or upon passing in close proximity to the device, e.g., a fixture, undergoes heat exchange with the device of the invention. This medium is then transferred to another heating or cooling element that either heats or cools the medium using any method or system known in the art, e.g., any method or system described herein. The electronic elements for temperature control may include one or more microcontroller, which stores the information about the desired temperature setpoint or range. The electronic elements for temperature control may also include one or more temperature detector (e.g., a thermocouple, thermistor, IR thermometer, etc.), which may be embedded in the device. The temperature detector detects the temperature of the environment and reports it to the microcontroller, which the microcontroller uses to determine whether any of the temperature control elements need to be activated to heat or cool the system. The microcontroller may control one or more of the temperature control elements (e.g., a heating element or a cooling element) as necessary according to the information received from the temperature detector (e.g., a thermocouple, thermistor, IR thermometer, etc.) according to any algorithm known in the art (e.g., PID, fuzzy logic, feed forward, neural networks, on-off, etc.). One or more fixtures may also contain one or more of the electronic elements for thermal control. The fixture(s) may further contain one or more electronic elements for radiofrequency generation.

The device may have a thermal insulation enclosure to improve further temperature control of the device (e.g., thermal homogeneity of magnets). The temperature control system is capable of keeping the device at a constant temperature of between about 20° C. to about 50° C. (e.g., about 30° C. to about 40° C.). The thermal insulation enclosure may also be included to to keep the device at a constant temperature of between about 20° C. to about 50° C. (e.g., about 30° C. to about 40° C.).

The device may also contain a printed circuit board (PCB), which may contain one or more variable capacitors (e.g., capacitors having capacitance of 1-30 pF). The PCB may be encased in an enclosure, which may be made of copper or aluminum. The capacitors on the PCB are used to store energy for the RLC circuit (especially, for generation of RF pulses). The device may further include an external connector, e.g., a connector linking the device to external power supply and controls (e.g., an external connector may be a subminiature version A (SMA) connector). The device may also contain grounding, an amplifier, and/or a computer. The processor of the device may be present in the computer, which may be separate from the portion of the device carried by or worn by the subject. Grounding can be any conductive material or a plurality of conductive materials linking the subject to the magnet or wiring (e.g., SMA connector) of the device of the invention.

The external power supply may be a stationary source of electricity, such as electrical mains (e.g., a 110V, 220V, or 250V socket) or a power adapter connected to the electrical mains (e.g., a power adapter converting AC 110V power supply to DC 5V power supply). The external power supply may be portable and may include a primary cell (e.g., a non-rechargeable battery) or a secondary cell (e.g., a rechargeable battery). For example, the battery may be a NiCd battery or a Li ion battery. The external power supply may also be a solar module, either alone or in combination with any battery. The portable power supply may be incorporated into the body of the device of the invention (internal power supply).

The devices of the invention can be used to determine a volume of any water compartment, such as an intracellular, an interstitial, or an extracellular compartment. Thus, devices of the invention for determining a vascular volume may also be used to determine an intracellular volume, an interstitial volume, or an extracellular volume of a water compartment other than a vascular volume.

Computer-Readable Storage Media of the Invention

The present invention provides non-transitory computer-readable storage media storing a computer program for converting a relaxation time decay curve collected from NMR measurement of the relaxation time of hydrogen nuclei in water in a tissue portion of a subject. The computer program contains a routine set of instructions for causing a computer to perform the steps of: (a) fitting a sum of one or more exponential curves to a measured decay curve, each exponential curve relating to one or more water compartments within the tissue portion of the subject, where the exponential curve contains a first constant and a second constant, the first constant being the relaxation time of hydrogen nuclei in water within the above-mentioned one or more water compartments, the second constant being a signal magnitude; (b) determining the first and the second constants from the fit; (c) comparing the first or the second constant to a reference relaxation constant. The reference constant can be a reference relaxation time or a reference peak intensity.

The computer program may contain a routine set of instructions for causing a computer to deconvolute raw relaxation data into a relaxogram, the latter having at least one, or all, resolvable components of the raw relaxation data as one or more peaks within a function of signal intensity and relaxation time. The routine set of instructions may further contain instructions for causing the computer to perform the steps of: (a) determining an area under the one or more peaks in the relaxogram, and (b) comparing the determined area to a reference peak area. In another example, the routine set of instructions may contain instructions for causing a computer to perform the steps of: (a) determining an intensity of one or more peaks in the relaxogram (e.g., performing a measurement of the peak height and/or peak width of a relaxation signal of the hydrogen nuclei), and (b) comparing the intensity of the one or more peaks to an intensity of one or more reference peaks.

In all of the above examples, the computer-readable storage media may further include data corresponding to an identification of, or data that identifies, the hydration state of a subject (e.g., the data may indicate the subject as being in a state of euhydration, dehydration, or water intoxication). The computer-readable storage media may also include data corresponding to the optimal treatment of the subject in view of the severity of an identified state, if the subject is identified to be in a state other than euhydration.

The routine set of instructions may also contain instructions for causing a computer to perform an algorithm according to one or more methods of the invention described herein.

All of the computer-readable storage media described herein exclude any transitory media (e.g., volatile memory, data signals embodied in a carrier wave, such as a carrier wave in a network, e.g., Internet). Examples of computer-readable storage media include non-volatile memory media, e.g., magnetic storage devices (e.g., a conventional "hard drive," RAID array, floppy disk), optical storage devices (e.g., compact disk (CD) or digital video disk (DVD)), or an integrated circuit device, such as a solid-state drive (SSD) or a USB flash drive.

The computer-readable storage media of the invention can be used to determine a volume of any water compartment, such as an intracellular, an interstitial, or an extracellular compartment. Thus, a computer-readable storage medium of the invention for use in determining a vascular volume may also be used to determine an intracellular volume, an interstitial volume, or an extracellular volume of a water compartment other than a vascular volume.

The following examples are meant to illustrate the invention. They are not meant to limit the invention in any way.

EXAMPLES

Example 1

Relaxation Analysis, Murine Whole-Body

This example demonstrates the feasibility of measuring hydration changes through the use of exponential regression fitting of raw NMR data. Mathematically, the two relaxation rates ($T_1$ and $T_2$) can be modeled with the following exponential equations:

$$M_{T1}(t) = \sum_{i=1}^{n} M_n\left(1 - e^{\frac{-t}{T1_n}}\right) \quad \text{(Eq. 1)}$$

and $$M_{T2}(t) = \sum_{i=1}^{n} M_n\left(e^{\frac{-t}{T2_n}}\right) \quad \text{(Eq. 2)}$$

where in both cases M is the signal magnitude, n is the number of components that make up the NMR signal. It should be noted that even though a sample may contain more than a single component—it can be modeled with a single component regression (n=1); however, there may be a larger fitting error that should be noted. In the most ideal situation, the exact number of components will be known and the correct n for the model will be used. To improve the accuracy of the multi-component regression fit; alternatively, a spectrum based approach may be more appropriate (described in Example 2).

Figure 3:
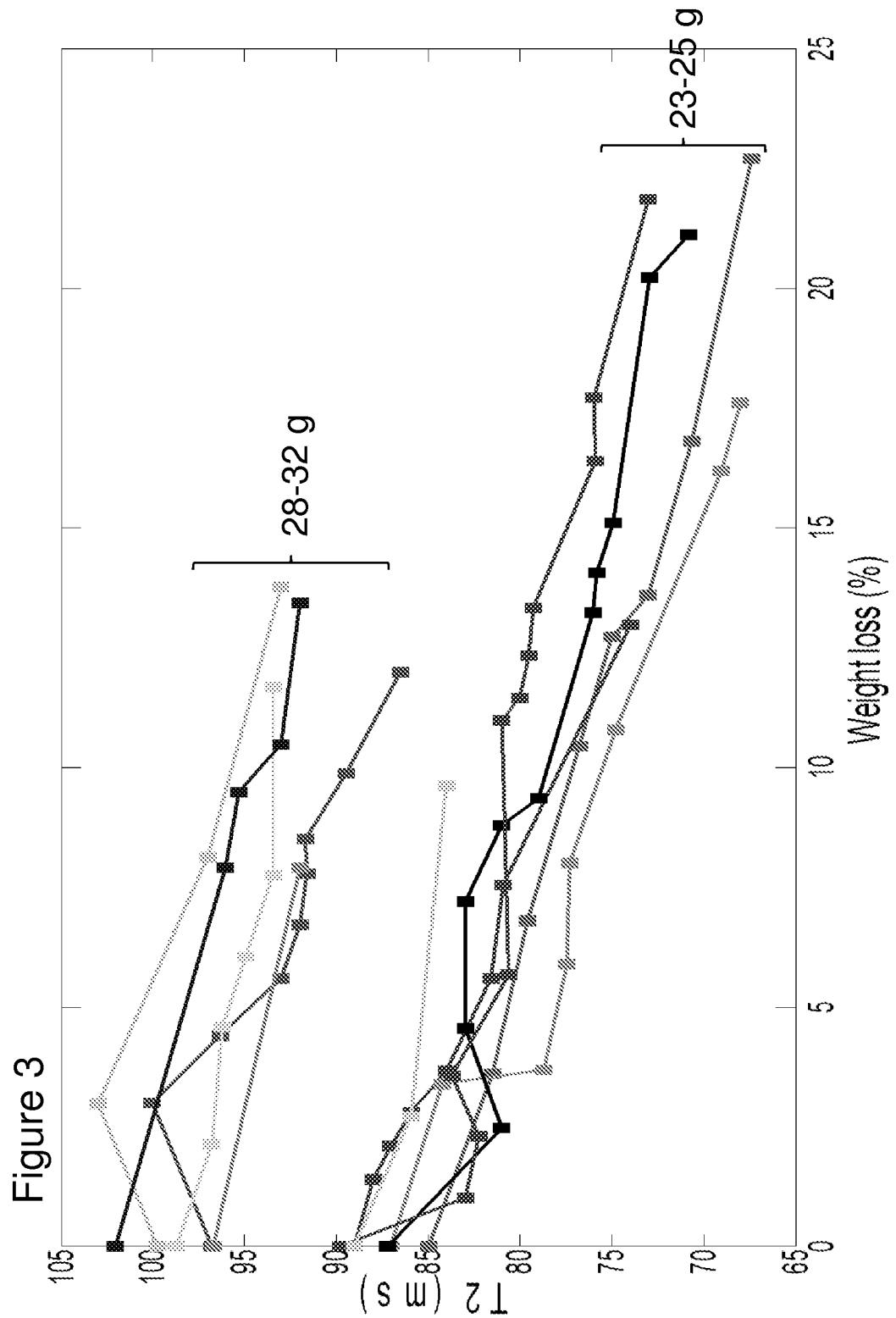
FIG. 3 is a graph showing a clear drop in $T_2$ as a function of weight loss (attributable to water loss). The clear segregation in two groups having different weight ranges (23-25 g and 28-32 g mice) is likely due to the different body compositions; older and heavier mice tend to have more adipose tissue and an overall longer relaxation time.

This single exponential fit (n=1) for $T_2$ was applied to a murine model of dehydration, which was accomplished through water restriction. The whole-body is comprised of numerous tissue systems, each with its own unique $T_1$ and $T_2$ relaxation times; it is considered a multi-exponential model. FIG. 3 serves as a prime example depicting the ability to model a multi-component system with a single component exponential function and still yield information rich data. One can clearly see a downward trend in measurements as a function of body weight changes (which are mainly attributed to water loss). Relaxation times become faster (downward trend) during dehydration because there is a loss in water, which has a longer relaxation time—there is decreased contribution from this long relaxation component that moves the aggregate relaxation time towards a faster relaxation.

The panel demonstrates a clear drop in $T_2$ as a function of weight loss (assumed to be mostly attributable to water loss). The clear segregation in groups (23-25 g and 28-32 g mice) is likely due to the different body compositions; older and heavier mice tend to have more adipose tissue and an overall longer relaxation time.

Example 2

Tissue-Specific Spectrum Analysis

Figure 4:
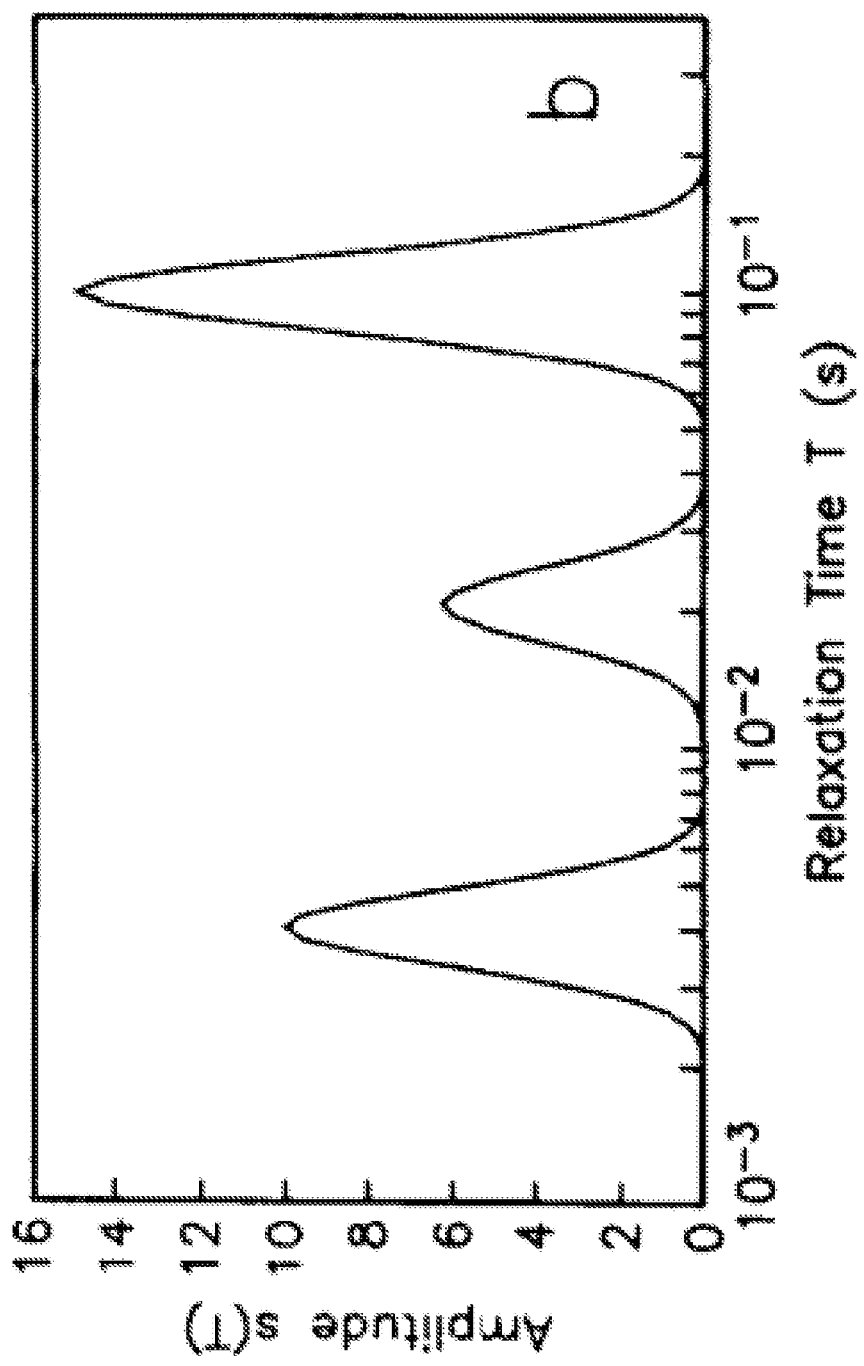
FIG. 4 is a graph showing synthetically generated NMR data deconvoluted into a relaxation distribution in a time domain. Each peak represents a separate component corresponding to a distinct water compartment. Along x-axis (log scale) are shown relaxation time values T (seconds). The curve (peaks) is a function of time with response values of signal intensity (amplitude). Reproduced from Whittal, K. P. and MacKay, A. L., (*J. Magn. Reson.* 84:134-152, 1989).

This example demonstrates the feasibility of measuring water content of discrete fluid compartments (intracellular, extracellular, interstitial, intravascular, etc.) of a given tissue through signal processing. Raw relaxation data can be deconvoluted into a relaxogram, FIG. 4. This method separates the $T_2$ relaxation data into all the resolvable components as a function of relaxation time and signal intensity. A major benefit to this method is the fact that the number of components need not be known for accurate analysts, in contrast to the exponential regression method previously described. As shown in FIG. 4, water location in various tissues and within different compartments of a tissue yields differences in measured relaxation rates and signal intensities.

Data deconvolution and multi-exponential regression analysis provide a level of resolution that facilitates the tracking of changes of different tissues and tissue compartments. The resolvable compartments may vary for different tissues and/or systems of tissues. The importance of this type of resolution is that different compartments respond in various ways to changes in hydration state. Thus, meaningful data can be obtained using various tissue portions and by tracking one or more water compartments in the tissue portions. Clinically relevant fluid compartments include the vasculature, intracellular, and extracellular spaces.

Figure 5:
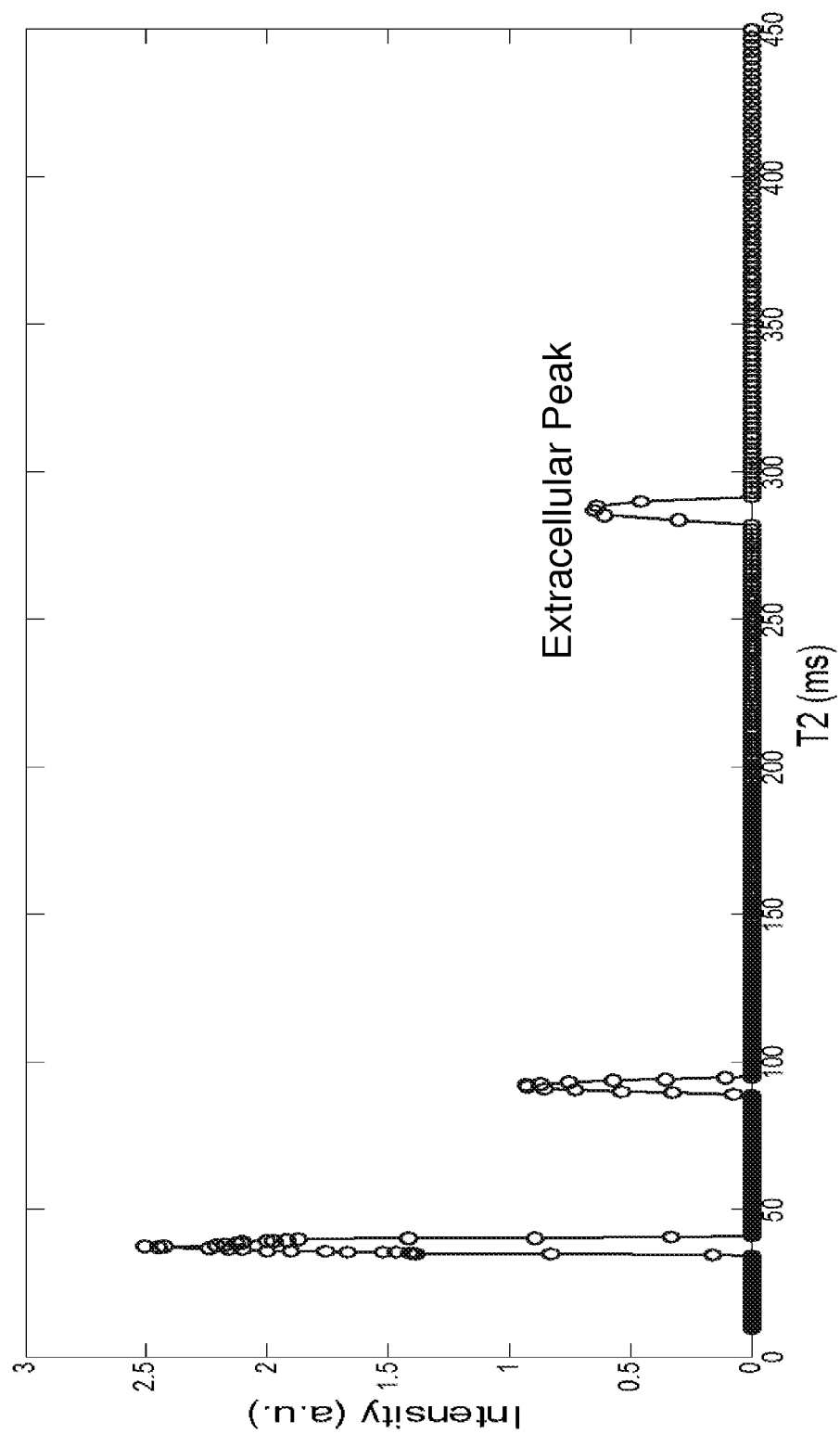
FIG. 5 is a graph showing a sample NMR spectrum of murine muscle. The first peak (from the left) is the intracellular water compartment, the second peak is postulated to be non-myocyte tissue (e.g., connective tissue), and the third peak is the interstitial water compartment (e.g., free water).
Figure 6:
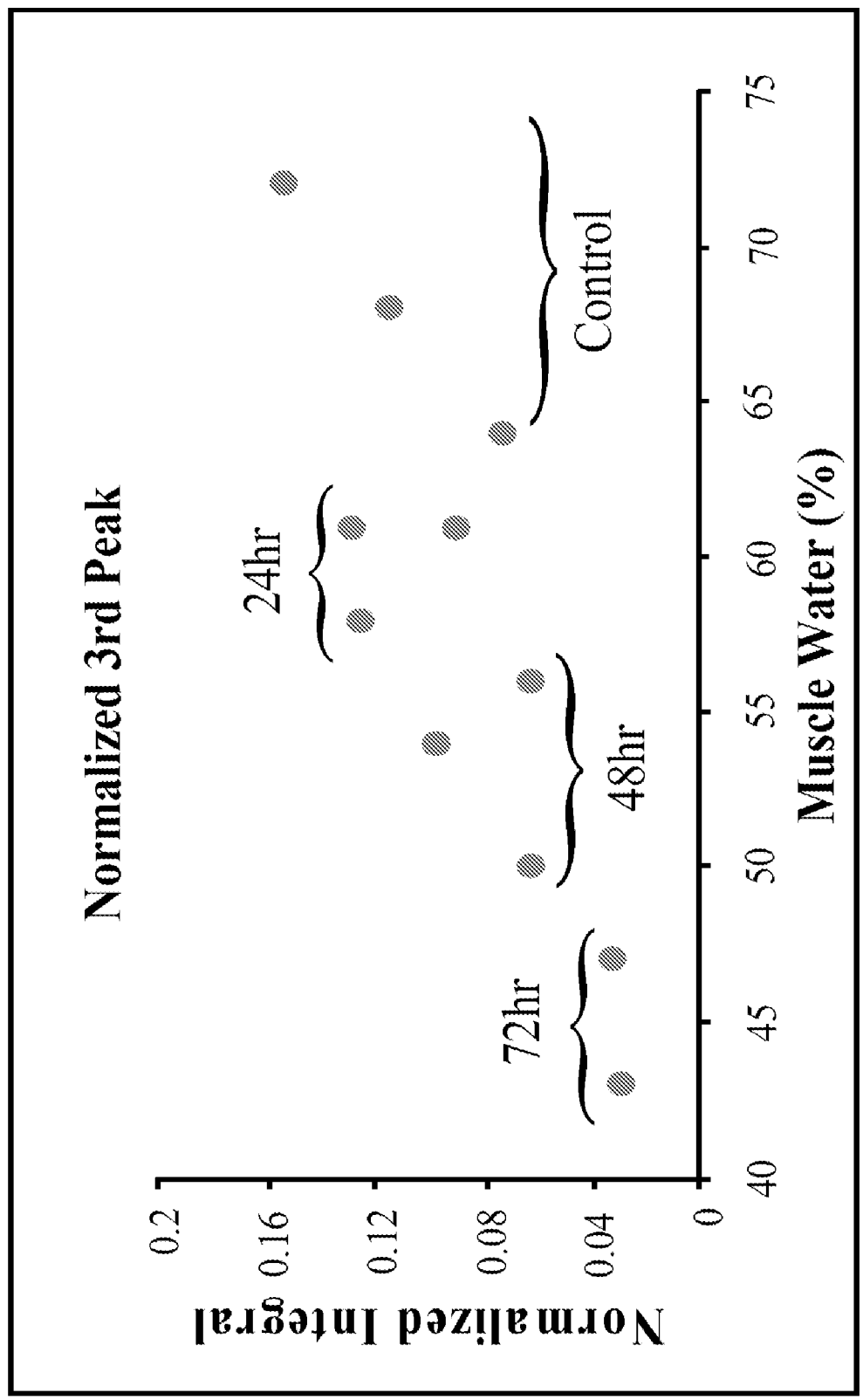
FIG. 6 is a graph showing a normalized plot of the third peak from FIG. 5 as a function of muscle water %. There is an apparent trend in the long relaxation time compartment (compartment corresponding to, e.g., interstitial water) as a function of water % composition. The water deprivation time is shown above the data points.

The same model of dehydration, described in Example 1, and NMR measurements were performed on excised muscle tissue. Water percentages of the muscle samples were calculated by performing wet weight-dry weight measurements. NMR analysis, described above, is capable of resolving three components in skeletal muscle. Extracellular water appeared to have the greatest change during dehydration, and thus became the focus peak (FIG. 5). Contrasting the previous description of single exponential fitting and comparing relaxation times, spectrum analysis provides a resolution in which the magnitude of the signal changes rather than the actual relaxation time. Thus, in FIG. 6, measurements are made with respect to the area under the peak rather than the relaxation time. The graph shows that the normalized signal intensity of the extracellular peak drops as muscle water percent decreases.

Example 3

Targeted Tissue Analysis—Intravascular Fluid Load Assessment in Humans

Figure 7:
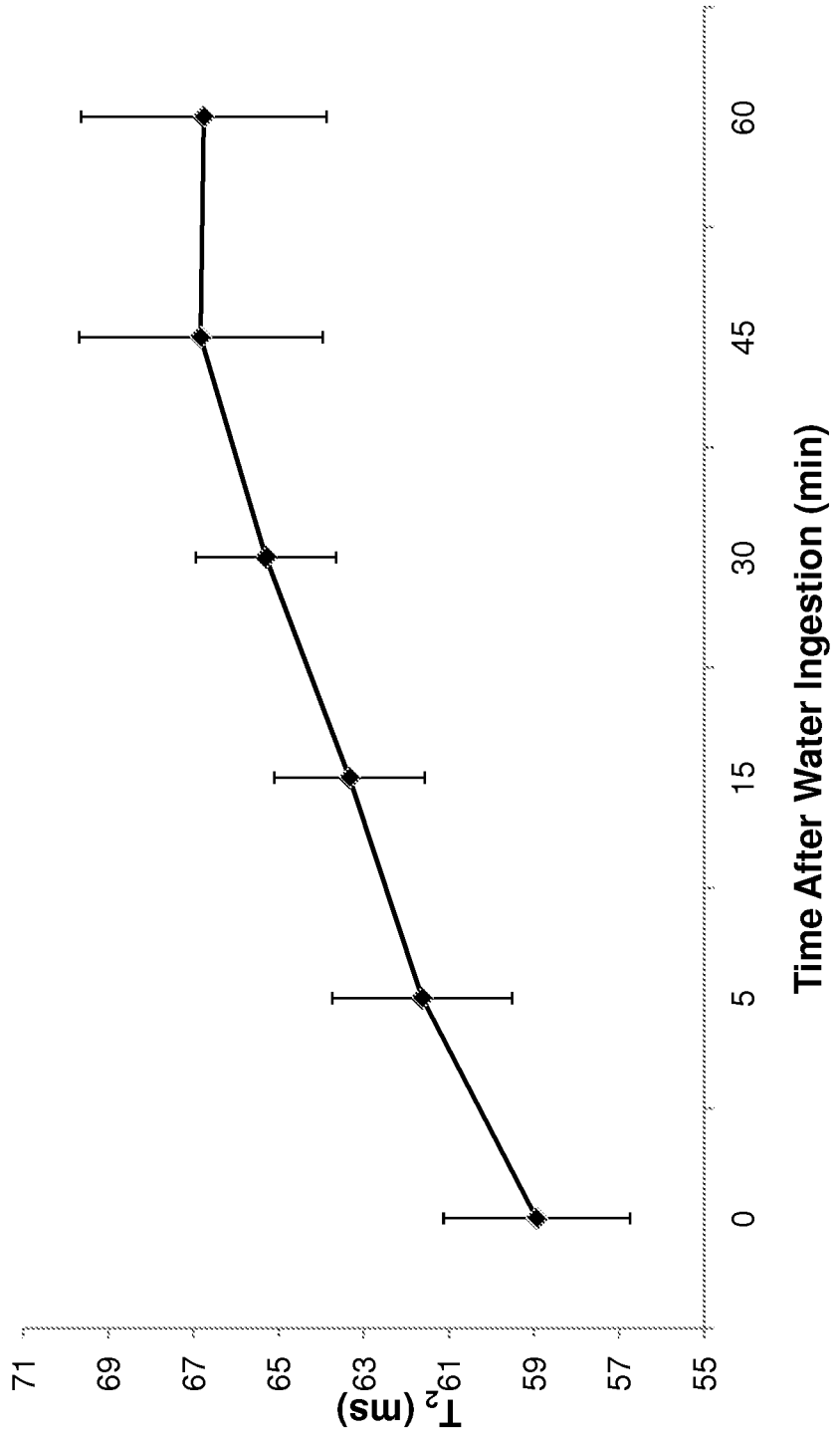
FIG. 7 is a graph showing $T_2$ response of the finger after ingestion of a 500mL water bolus. There exists a clear upwards trend which reflects an increased presence of measured water (which has a long $T_2$ relaxation time). Analysis was performed using single-exponential regression fitting.

This example illustrates the feasibility of assessing hydration state by NMR measurement of a specific anatomic location. Different anatomic locations are composed of different tissue types/fluid compartments and some locations may be more sensitive to changes in hydration than others. A custom NMR sensor was designed and constructed to perform relaxation measurements on the finger because we were interested in measuring intravascular water content. Changes in the intravascular water content were measured by ingesting 500 mL of water within 2 minutes (water bolus). Finger measurements were taken at time points up to 1 hour after ingestion. FIG. 7 depicts an upward trend as a function of time after water ingestion. As described previously, a single exponential regression was employed to assess the acquired data.

Figure 8:
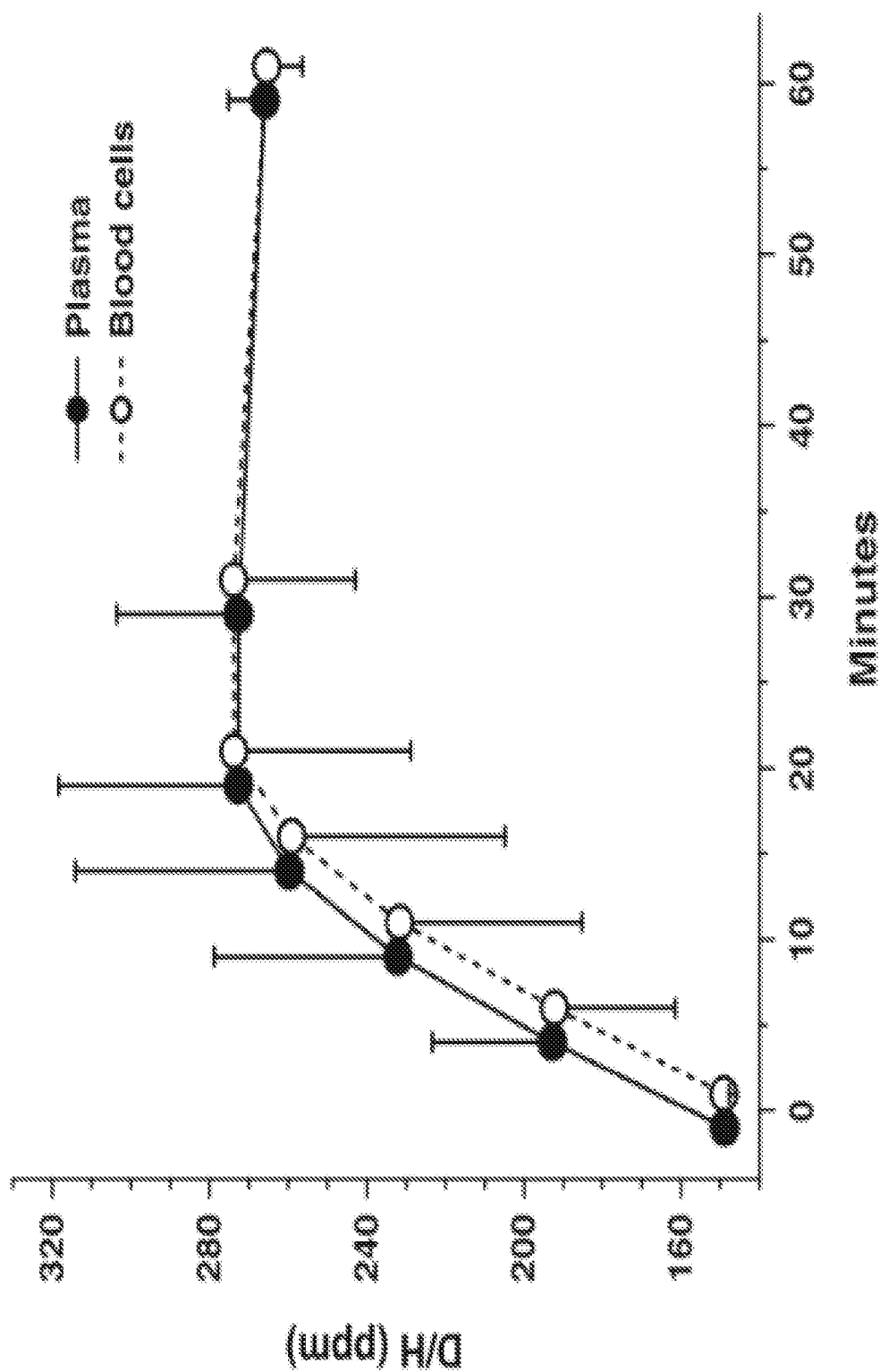
FIG. 8 is a graph showing plasma and blood cell deuterium to protium ratio (D/H) over a 60 minute period after ingestion of labeled water. There is a clear upward trend in D/H ratio as a function of time after water ingestion. Reproduced from Peronnet et al. (*Eur. J. Apl. Physiol.* 112:2213-2222, 2012).

The trends evident in these noninvasively-obtained results line up with results from another study where subjects drank deuterium-labeled water and then had blood draws taken over a 60 minute period to measure the ratio of labeled to unlabeled water in their vasculature (see FIG. 8).

Example 4

Hydration State Assessment in Humans

In this Example, hydration states of human subjects (three males and one female) were analyzed pre- and post-exercise induced dehydration. The hydration states were assessed using the NMR device (0.55 T device) having 40 wedge-shaped NdFeB magnets arranged in a circular Halbach array, which is described further below. Subjects underwent exercise-induced dehydration. It was known that individuals that perform exercise undergo dehydration. Thermogenesis occurs due to increases in metabolic rate. This causes sweating. Increases in respiration rate, due to increased oxygen demand, also lead to water loss from the respiratory tract.

These dehydration experiments only involved two finger measurements for each participant: pre and post-exercise. Pre-exercise measurements were performed on the index finger of a subject in a seated position. Subjects were then allowed to perform their routine exercise without any interventional guidance from the investigators. It was noted that each participant lost approximately 1 pound (participant weight range: 110-140 lbs) with no exercise period taking longer than an hour. All weight change was associated with water loss. Any weight loss contribution from metabolic or catabolic (highly unlikely) was at a minimum given the acute nature of each exercise. All subjects also reported no intake of water during exercise or prior to the post-exercise measurements. Post-exercise measurements were performed approximately half an hour after cessation of physical activity to allow for bodily equilibration to rest and the environment.

Figure 13:
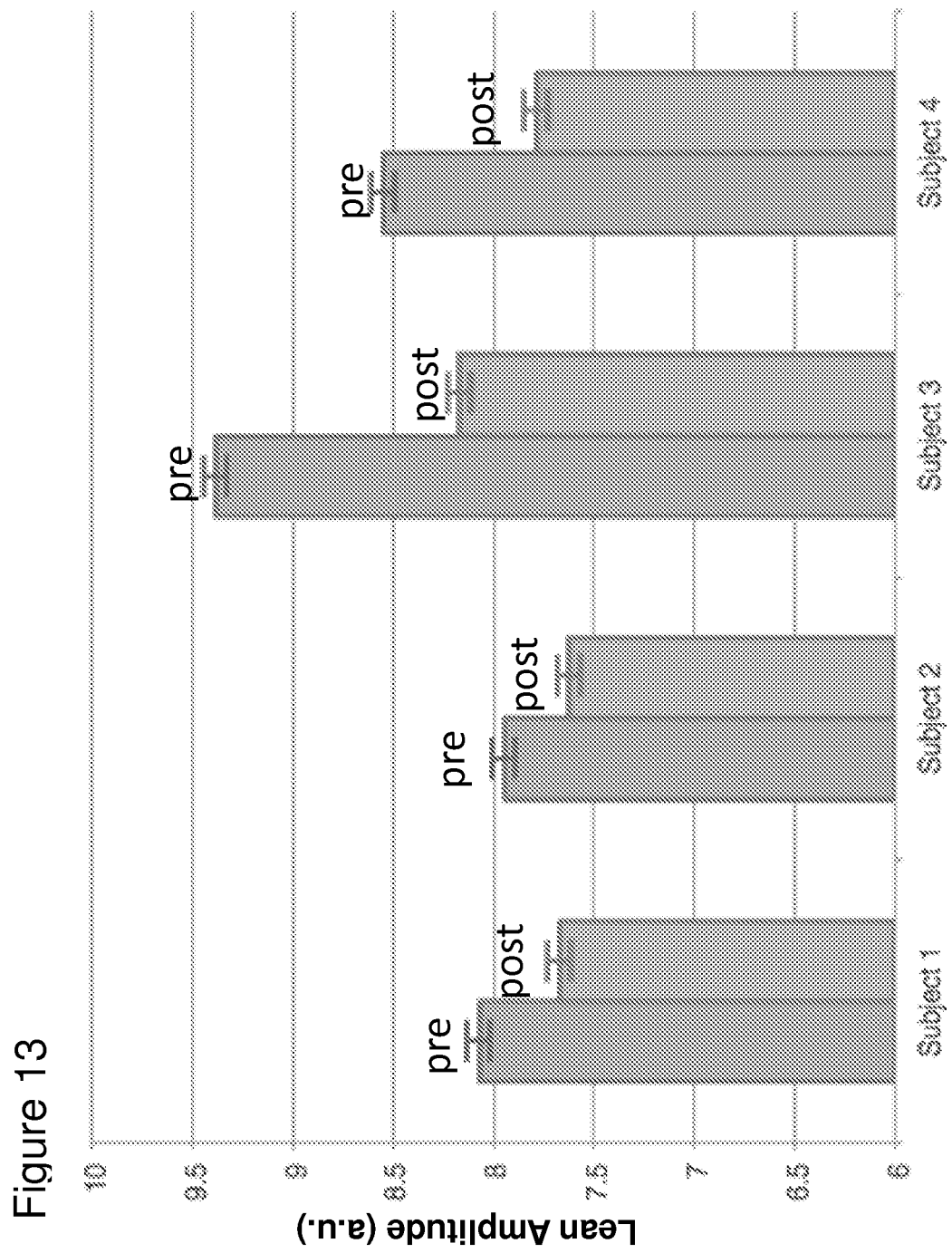
FIG. 13 is a chart showing the NMR signal magnitudes derived from $T_2$ measurements on fingers of subjects before (pre) and after (post) exercise-induced dehydration. Subjects 1, 3, and 4 are males, and subject 2 is a female. The y-axis shows the signal magnitude for the measured compartment (lean amplitude), as measured in arbitrary units.

It is possible to separate out various tissues of interest using methods described above (e.g., multi-exponential regression analysis). FIG. 13 demonstrates clear drops in a single compartment of the tissue signal amplitude between pre and post exercise measurements. NMR signal amplitudes correlate to the amount of material present within a given measurement region. The drop in signal amplitude is indicative of water loss from the tissue. Variation in the amount of signal change likely arises from inherent physiologic heterogeneity between study participants.

This finding is consistent with previous physiologic studies in rats and humans that used empirical, non-NMR methods. Some studies demonstrated that the largest tissue contributor to water loss during dehydration is a lean tissue (Nose et al., *Jpn J. Physiol.*, 33:1019-1029, 1983; Costill et al., *J Appl Physiol.*, 40:6-11, 1976).

Example Experimental Hardware

Figure 9:
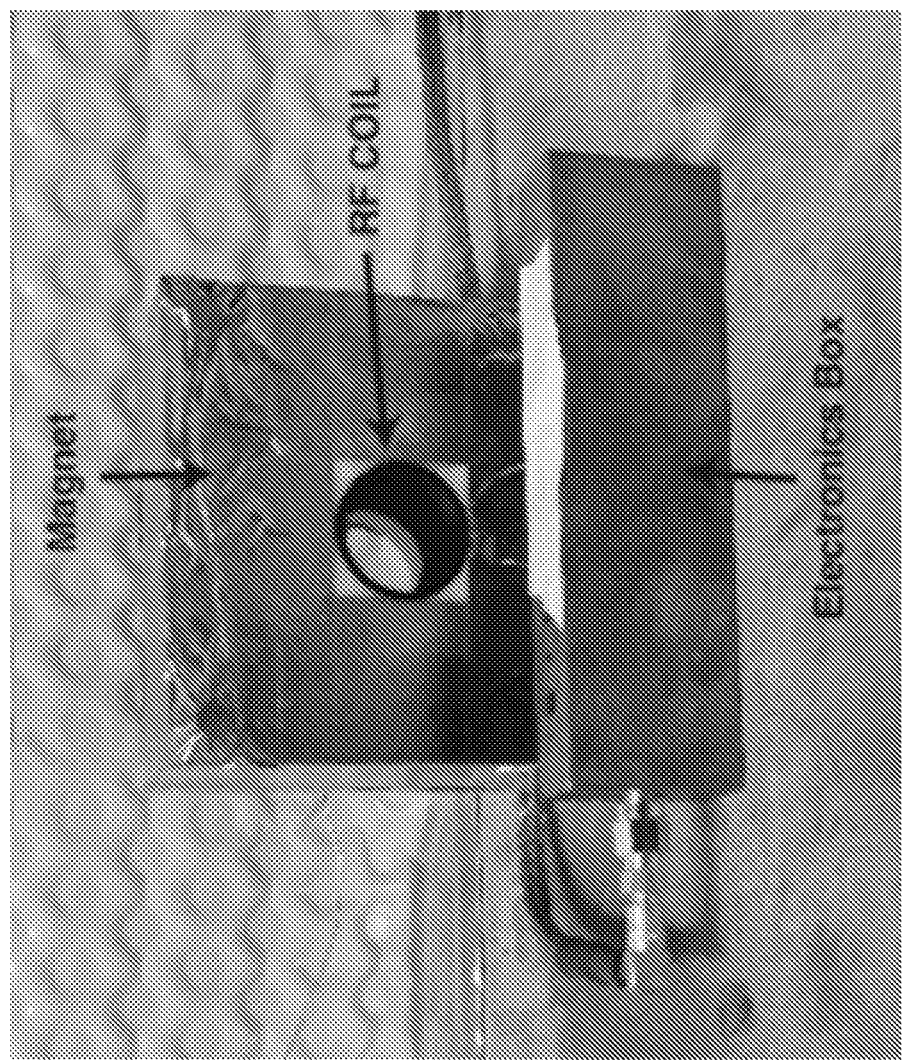
FIG. 9 is a photograph showing the setup of an exemplary device of the invention, which includes a magnet, an electronics box containing tuning capacitors, and an RF coil (an inductor of an RLC circuit) (black region concentric with the open bore).
Figure 10:
FIG. 10 is a photograph showing an experimental setup for finger measurements. A copper grounding surface is shown (labeled as "Copper Grounding Surface").

Execution of Example 3 was accomplished through a custom NMR system with critical components including: magnet, RLC circuit, grounding element, and thermal control (FIGS. 9 and 10).

Magnets

Figure 11:
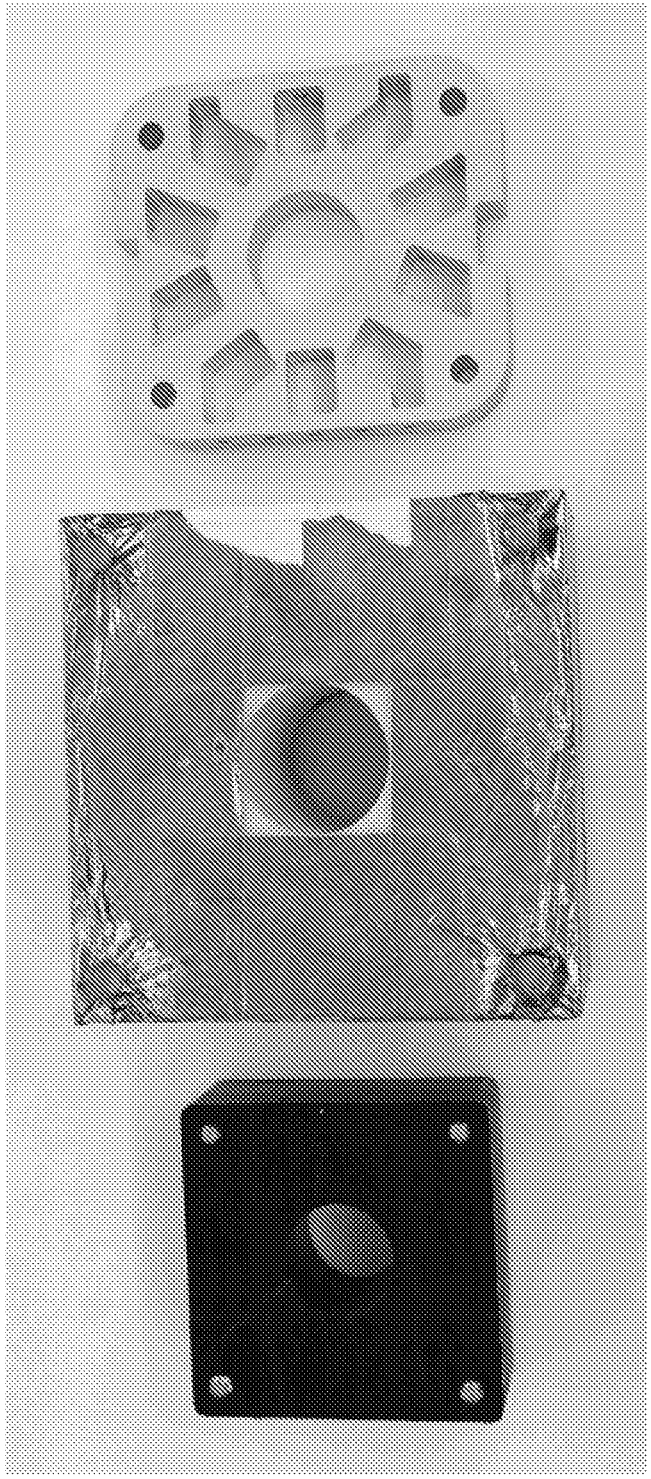
FIG. 11 is a photograph showing two devices of the invention (A and B) and a fixture (C). Device A contains 16 cuboidal permanent magnets arranged within 2 stacked fixtures and enclosed within a plastic enclosure. Device B contains 72 cuboidal permanent magnets arranged within 3 stacked fixtures and enclosed within a copper enclosure. Fixture C is a component of a device containing 40 magnets arranged in 4 stacked fixtures. Overall magnetic field strengths and dimensions are shown for each device.

In one embodiment, the magnet contains 72 cuboidal, N52 NdFeB rare earth magnets arranged in 3 stacks of circular Halbach arrays (see Device B in FIG. 11; for Halbach arrays see Halbach, *Nuclear Instruments and Methods* 169:1-10, 1980). The central field strength is about 0.4 T at about 25° C. In other embodiments, the configurations can include a magnet arrangement that produces a uniform central region, but may vary the number of magnets used (2-100 total magnets), source of magnetic field (any make of rare earth magnet, electromagnet, pulsed electromagnet, or earth's magnetic field up to 2 T field strength), and shape of magnets to be used (any cylindrical or polygonal shape). In another embodiment, the magnet contains 40 individual, 0.375" cuboidal N52 grade NdFeB magnets arranged in 4 stacks of circular Halbach arrays (10 magnets per stack; the magnet was constructed using Fixture C shown in FIG. 11). The individual magnets closely circumscribe a central bore region of 0.9"; measurements were performed within this bore. The central field strength is about 0.22 T at about 25° C. In yet another embodiment, the magnet contains 40 individual, 1" length, 0.5" height, 45° wedge shaped N52 grade NdFeB magnets arranged in 4 stacks of circular Halbach arrays (10 magnets per stack; the magnet was constructed using Fixture C shown in FIG. 11). The individual magnets closely circumscribe a central bore region of 0.9"; measurements are performed within this bore. The central field strength is about 0.55 T at about 25° C.

Figure 12:
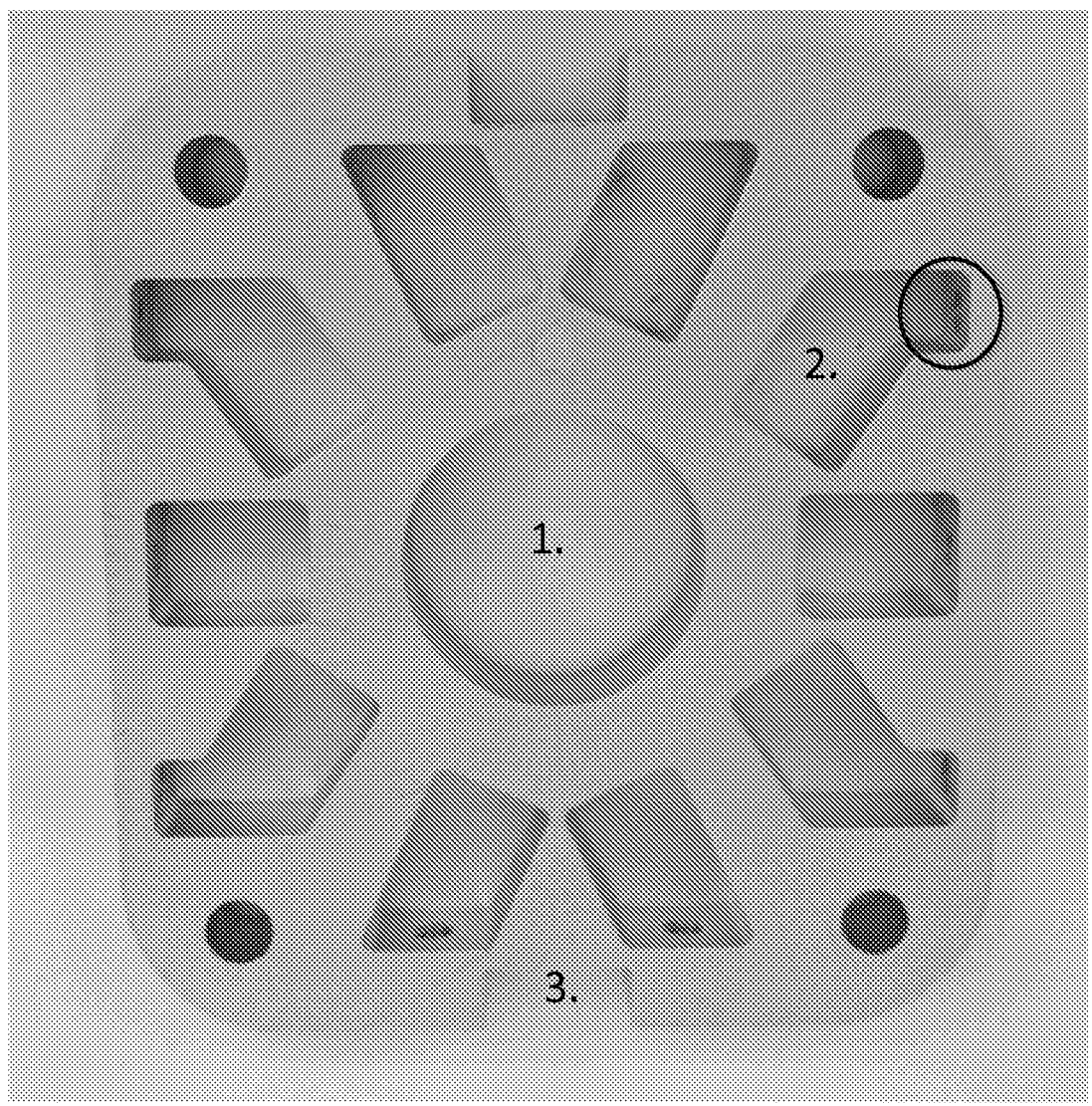
FIG. 12 is a photograph showing a detailed view of Fixture C shown in FIG. 11. 1 is an inner bore measuring 0.9". 2 is a magnet pocket that is angled and oversized to accommodate mechanical shims and that has a circled hole for a screw capable of securing and moving mechanical shims. 3 is a mounting location for a thermal control element.

Fixtures that hold the magnets may be constructed from an acetal copolymer. Other devices can be made from metal (any non or minimally magnetic metal or alloy) and/or other plastics (PTFE, PCTFE, ABS, Polycarbonate, PEEK). Fixtures may also have integrated heating elements to help maintain an optimal magnet operating temperature. Electronic elements for radiofrequency generation and/or thermal control may be integrated within the fixture as well to minimize the number of physically separate system components. For examples of fully assembled fixtures and magnets see Devices A and B in FIG. 10. An exemplary fixture can be found in FIG. 11 (Fixture C) and FIG. 12.

The magnet configuration can have a central region through which to insert/fit a tissue portion (e.g., a finger) for measurement. The Halbach configuration is preferred, but any arrangement that produces a region of high uniformity where the sample is to be measured is amenable.

RF Coil/RLC Circuit

The example RF coil utilizes insulated 32 AWG copper wire with a thirteen-turn inductor wrapped around an acetal copolymer bobbin (see, e.g., FIG. 9). A custom PCB and copper enclosure house the variable capacitors (1-30pF). A subminiature version A (SMA) connector provides connection to external power supplies and controls.

Grounding

Grounding includes a copper cloth clad acrylic board (see, e.g., FIG. 10). This board is electrically connected with conductive tape to the (SMA) wiring to the copper board—this ensures a common ground between the system and the individual being measured.

Thermal Control

The aforementioned device can be kept at constant temperature (30-40° C.) by a temperature control system, as described above.

Device Comparison

The 0.22 T and 0.55 T devices were compared to one another to determined performance gains. A sample of copper sulfate solution was used for all measurements and can be easily modeled as a single exponential. A single exponential fitting method was used to obtain the root mean squared error (RMSE), which can be interpreted as the noise in the system. Signal to noise ratio (SNR) was calculated by dividing the signal amplitude (Amp) by the noise (RMSE).

A higher SNR signifies improved performance gains. The results of this comparison are shown in Table 1 below.

TABLE 1

|       | Amp | RMSE | SNR   |
|-------|-----|------|-------|
| 0.22T | 15  | 0.14 | 107   |
| 0.55T | 295 | 0.21 | 1,404 |

Other Embodiments

All publications, patents, and patent applications mentioned in the above specification are hereby incorporated by reference. Various modifications and variations of the described device and methods of use of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

The invention claimed is:

1. A method of treating systemic dehydration or systemic overhydration in a subject, the method comprising
   (a) exposing a tissue portion comprising a lean tissue of the subject in vivo to a magnetic field and RF pulse from a nuclear magnetic resonance device to excite hydrogen nuclei of water within the tissue portion comprising an extracellular water compartment,
   (b) in the absence of a contrast agent, measuring a $T_2$ relaxation time of the hydrogen nuclei in the tissue portion using the nuclear magnetic resonance device to produce $T_2$ relaxation time data,
   (c) deconvoluting the $T_2$ relaxation time data using multi-exponential regression analysis to produce a signal amplitude for the extracellular water compartment and determining the subject as (i) having systemic dehydration if the signal amplitude is decreased relative to a reference signal amplitude or (ii) having systemic overhydration if the signal amplitude is increased relative to the reference signal amplitude, wherein steps (a), (b), and (c) are non-invasive, and wherein the reference signal amplitude is produced by a reference measurement in the absence of a contrast agent comprising one or more prior measurements of the $T_2$ relaxation time of hydrogen nuclei of water in the tissue portion of the subject in the state of systemic euhydration, and
   (d) treating systemic dehydration in the subject determined as having systemic dehydration or treating systemic overhydration in the subject determined as having systemic overhydration.

2. The method of claim 1, wherein the steps (a) and (b) are repeated two or more times.

3. The method of claim 1, wherein the subject has a disease or condition that increases the risk of having, or results from, dehydration or overhydration.

4. The method of claim 3, wherein the subject has a disease or condition selected from the group consisting of congestive heart failure (CHF), renal failure, liver cirrhosis, nephrotic syndrome, brain swelling, diabetes, staphylococcal infection, nephrolithiasis, diarrhea, colitis, preferably ulcerative colitis, pyelonephritis, cystic fibrosis, Huntington's disease, rotavirus infection, herpangina, salmonellosis, norovirus infection, pertussis, cryptosporidium infection, cholera, coma, and water intoxication; wherein the subject has, or is suspected of having, congestion or hemodilution: wherein the subject has at least one symptom of congestion selected from the group consisting of dyspnea, orthopnea, exercise intolerance, pathologic S3 or S4 heart sounds, tachycardia, tachypenia, jugular venous distention, peripheral edema, ascites, and increased filling pressures of the heart.

5. The method of claim 3, wherein the subject has congestive heart failure, liver failure, renal failure, Cushing's syndrome, or pulmonary congestion.

6. The method of claim 1, wherein the tissue portion is a peripheral body part.

7. The method of claim 1, wherein the method is performed on a tissue volume of at least 0.01 cm$^3$.

8. The method of claim 1, wherein the method is performed on a tissue volume of at most 20.0 cm$^3$.

9. The method of claim 7, wherein the device is configured to provide a substantially homogeneous magnetic field over said volume.

10. The method of claim 1, wherein the $T_2$ relaxation time is measured using single-voxel spectroscopy (SVS).

11. The method of claim 1, wherein the $T_2$ relaxation time is measured using multi-voxel spectroscopy.

12. The method of claim 1, wherein the device is configured to be in close proximity to the tissue of the subject.

13. The method of claim 1, wherein the device is portable, hand-held, wearable, or is attached to the tissue portion.

14. The method of claim 1, wherein the device comprises (a) one or more magnets, (b) an RLC circuit, and (c) a processor.

15. The method of claim 14, wherein the processor is capable of (i) determining relaxation time of the hydrogen nuclei and (ii) comparing the determined signal amplitude to a reference signal amplitude.

16. The method of claim 1, wherein the step of treating dehydration comprises oral rehydration therapy or fluid replacement therapy.

17. The method of claim 1, wherein the step of treating overhydration comprises administering a diuretic, a beta-blocker, an angiotensin-converting enzyme (ACE) inhibitor, a vasopressin receptor antagonist, or a combination thereof.

18. The method of claim 1, wherein the step of treating overhydration comprises blood ultrafiltration.

19. The method of claim 1, wherein the subject is selected from the group consisting of an elderly subject, a child, an athlete, a soldier, an aircraft pilot, an air traffic controller, a locomotive engineer, and a crane operator.

20. The method of claim 1, wherein the tissue portion is or is within the subject's finger, ear, nose, cheek, toe, foot, calf, hand, wrist, leg, or arm.

* * * * *